(12) United States Patent
Gundel et al.

(10) Patent No.: US 6,780,818 B2
(45) Date of Patent: Aug. 24, 2004

(54) QUANTITATIVE ORGANIC VAPOR-PARTICLE SAMPLER

(75) Inventors: Lara Gundel, Berkeley, CA (US); Joan M. Daisey, Walnut Creek, CA (US); Robert K. Stevens, Raleigh, NC (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/832,755

(22) Filed: Apr. 10, 2001

(65) Prior Publication Data

US 2001/0045000 A1 Nov. 29, 2001

Related U.S. Application Data

(60) Division of application No. 09/088,593, filed on Jun. 2, 1998, now Pat. No. 6,226,852, which is a continuation-in-part of application No. 08/191,344, filed on Feb. 2, 1994, now abandoned.

(51) Int. Cl.⁷ .............................................. B01J 20/26
(52) U.S. Cl. ........................................................ 502/402
(58) Field of Search ........................ 423/461; 502/401, 502/402

(56) References Cited

U.S. PATENT DOCUMENTS 3,974,227 A * 8/1976 Berthoux et al. .......... 502/162
4,128,513 A * 12/1978 Errede et al. .................. 521/50
4,900,520 A * 2/1990 Behnam et al. ............... 423/22

* cited by examiner

*Primary Examiner*—Stuart L. Hendrickson
(74) *Attorney, Agent, or Firm*—Hana Verny

(57) ABSTRACT

The present invention concerns a quantitative organic vapor-particle sampler which can efficiently sample both semi-volatile organic gases and particulate components through the use of a unique sorbent resin coating and process.

The sampler of the present invention comprises in its broadest aspect a tubular device having an inlet at one end through which organic vapor/particles are introduced, an outlet at the other end through which gases exit, at least one annular denuder interposed there between which is coated on the inside surface of the annulus with a specially prepared resin absorbent, which selectively absorbs organic vapors contained in the gases introduced into the inlet, and a filter which traps and collects particles.

The invention further concerns a semi-volatile organic reversible gas sorbent for use in an integrated diffusion vapor-particle sampler comprising macroreticular resin agglomerates of randomly packed microspheres with the continuous porous structure of particles ranging in size between 0.05–10 μm.

14 Claims, 8 Drawing Sheets

QUANTITATIVE ORGANIC VAPOR-PARTICLE SAMPLER

This is a Divisional application of Ser. No 09/088,593, filed on Jun. 2, 1998, now U.S. Pat. No. 6,226,852, which is a Continuation-In-Part application of abandoned U.S. Ser. No. 08/191,344 filed Feb. 2, 1994.

This invention was developed under National Heart, Lung, and Blood Institute of the Department of Health and Human Services, AREAL, and the U.S. Environmental Protection Agency grants. The U.S. Government has certain rights in this invention.

BACKGROUND OF THE INVENTION

1. Field of the Invention

The present invention concerns a quantitative organic vapor-particle sampler which can efficiently sample both semi-volatile organic gases and particulate components through the use of a unique sorbent resin coating and process.

The sampler of the present invention comprises in its broadest aspect a tubular device having an inlet at one end through which organic vapor/particles are introduced, an outlet at the other end through which gases exit, at least one annular denuder interposed therebetween which is coated on the inside surface of the annulus with a specially prepared resin absorbent, which selectively absorbs organic vapors contained in the gases introduced into the inlet, and a filter which traps and collects particles.

The invention further concerns a semi-volatile organic reversible gas sorbent for use in an integrated diffusion vapor-particle sampler comprising macroreticular resin agglomerates of randomly packed microspheres with the continuous porous structure of particles ranging in size between 0.05–10 $\mu$m.

2. Background and Related Disclosures

Assessment of both the vapor and particle components of various samples is important in a number of different situations. Accurate measurements of phase distributions of polycyclic aromatic hydrocarbons (PAH) in indoor air and environmental tobacco smoke (ETS) are needed in order to assess exposure or danger of exposure to carcinogenic compounds since lung deposition patterns of PAH depend on the distribution of the PAH between the gas and particle phases. Environmental fates of semi-volatile organic species are also phase-dependent because atmospheric reactions, and transport and deposition processes differ for gas and particulate semi-volatile species. Understanding the contribution of organic species to visibility degradation requires accurate phase distribution data. Pollutant control strategies are also phase-dependent.

Classic vapor-particle samplers, generally termed filter-sorbents, allow flow of an air sample through a chamber. In these samplers, at the end of the chamber where the airstream enters the chamber is a physical filter that picks up the particulate matter from the sample, as well as any semi-volatile components associated with it. At the base of the chamber is a sorbent bed which then collects any remaining gas phase materials. These gas-phase materials are then desorbed and analyzed to determine the presence of the material in the sample.

Some specialized filter-sorbent samplers which can detect gas-phase organic polycyclic aromatic hydrocarbons (PAH) have been developed. Cotham et al., developed such a sampler using polyurethane foam for the sorbent (*Environmental Science and Technology*, Vol 26, pp 469–478, (1992)). Kaupp et al used macroreticular polymeric resin beads to test for PAH, which are described in (*Atmosoheric Environment*, Vol 26A, pp 2259–2267, (1992).

Unfortunately, because these prior art sampler sorbent beds are positioned downstream from the filter, desorption of semi-volatile compounds from the filter creating negative artifacts, or collection of gases by the filter creating positive artifacts, lead to incorrect measurements of gas-phase and particle-phase concentrations. Considerable experimental and theoretical efforts have been expended to understand and correct for these condensation and vaporization effects.

An important advance in vapor-particle samplers was described by Possanzini in *Atmospheric Environment,* 16:845–853, (1983). The sampler described therein was able to test for inorganic acidic or basic gases using sorbents, such as sodium bicarbonate and citric acid. Additionally, Possanzini developed a different configuration for the sampler, allowing for greater efficiency while avoiding many of the problems of the prior art samplers.

In contrast to the prior art samplers, in Possanzini's configuration the sample is pulled through an annular space coated with a specific sorbent. The filter to collect the particulate portion of the sample is positioned downstream of the sorbent. This configuration obviates the positive and negative artifact problem of the prior art samplers.

The Possanzini configuration allows this arrangement because of the design and function of his sampler. Possanzini's sampler includes an annulus through which the sample flows by positioning two tubes concentrically to form such annulus. Other researchers have developed alternate means to produce the sample flow necessary for this sampling technique.

Broadly, Possanzini's improvement works as follows. When an airstream containing gases and particles is moving through tubes under conditions of laminar flow at a certain linear velocity, the particles move at the linear flow velocity. By contrast, the gases diffuse randomly in all directions at speeds determined only by their molecular weights and the temperature (kinetic energy).

When the airstream flows through an annulus, the dimension of the annulus (or annuli) is designed to be close to the diffusion path length of the gases. This results in the gases reaching the coated walls of the denuder where they react in an acid-base reaction. The gases are thus removed from the airstream, while the particle portion of the sample proceeds at the linear flow velocity of the airstream, to be removed by filtration. Any species desorbed from the filter are collected downstream of the filter.

The research community was very interested in sampling organic gases with the clearly superior efficiency using the Possanzini sampler. However, without a specific sorbent for organic components, this was not possible. Prior to the present invention, gaseous organic components could not be desorbed to make them available for analysis, much less to allow quantitative analysis.

Krieger et al (*Environ. Sci. Technol.*, Vol 26 pp 1551–1555, 1992) developed a diffusion denuder to fill the need for quantitative analysis of semi-volatile gases, but due to its small size, this denuder had no capacity to test the particulate phase of a sample.

Krieger's diffusion denuder uses capillary gas chromatographic stationary phase columns that can be used for direct determination of gas-phase semi-volatile organics. This denuder is very effective at quantifying volatile organic compounds but less effective at quantifying semi-volatile organic compounds. This denuder has a lower capacity for gas-phase organic compounds than the integrated organic vapor-particle sampler of the instant invention.

In order to gain some of the advantages of the Possanzini approach for gaseous organic component analysis, some other differential diffusion samplers were developed where a sorbent was used only to clean the sample stream of volatile organic compounds, rather than serve in any testing capacity. In these systems, two separate sample chambers had to be constructed in order to test two aliquots of each sample, one with and one without the non-reversible sorbent present. Typically each side also had a sorbent downstream of the filter. It was then hoped that the difference in the collection on the filters and downstream denuders from each system would reflect the gaseous semi-volatile organic component of the sample. There was no quantitative finding available for any particular species in this "cleanse and test" system.

More recently, some other denuders were developed, such as, for example denuder, to cleanse the sample stream of semi-volatile organic species described in Environ. Sci. Technol., Vol 22 pp 941–947, (1988). Coutant et al, developed silicon grease (Atm. Environment, Vol. 26A pp 2831–2834, 1992) and Eatough et al, used filter paper impregnated with activated carbon as a denuder coating to collect semi-volatile organic compounds and pesticides (Atm. Environment, Vol. 27A pp 1213–1219, (1993)). Differential samplers represent an important advance over conventional samplers in the assessment of organic, gaseous species. However, as seen in U.S. Pat. No. 5,302,191, issued Apr. 12, 1994, sampling of atmospheric semi-volatile compounds remains a challenge, and is often inappropriately addressed by atmospheric chemists.

Recently, materials such as various resins have been utilized for coating surfaces of vapor-particle samplers, described above.

Meitzner in U.S. Pat. No. 4,224,415, incorporated hereby by reference, discloses a method of making a macroreticular resin by copolymerizing a mixture consisting of a monovinyl carbocyclic aromatic compound or an ester of acrylic or methyacrylic acid, with a polyethylenically unsaturated monomer selected from the group consisting of a polyvinyl carbocyclic aromatic compound, an ester of a dihydric alcohol and an $\alpha$-$\beta$-ethylenically unsaturated carboxylic acid, diallyl malcate, and divinyl ketone. The copolymerization was conducted while the monomers were dissolved in 25 to 150% by weight, based on monomer weight, of an organic liquid or mixture of organic liquids which acts as a solvent for said monomers but are unable to substantially swell the copolymers resulting from copolymerization.

However, these resins were not successfully utilized for efficient sampling of semi-volatile organic gases and particulate components and there still remain daunting limitations to the current integrated sampler technology in assessing volatile and semi-volatile gas species in a sample. While differential samplers address some of these needs, they require double equipment, and they require, as a prerequisite to obtaining correct results, that the sample be divided perfectly. Because the species in question is never directly recovered, it is impossible to achieve accurate quantitative results for any particular gaseous organic component.

A sorbent which can be adhered to the inner surface of an integrated sampler, and from which volatile and semi-volatile organic components can be desorbed and assessed quantitatively, would represent an important and dramatic advancement in atmospheric sampling.

SUMMARY OF INVENTION

It is one object of this invention to provide an improved integrated vapor-particle sampler, for the purpose of sampling semi-volatile polycyclic aromatic hydrocarbons and other organic species, which is more efficient than the samplers of prior art.

It is another object of the invention to provide an integrated vapor-particle sampler which eliminates artifacts in the sampling procedure.

It is another object of the invention to provide an integrated vapor-particle sampler which contains as a component thereof an improved annular denuder.

It is another object of the invention to provide an integrated vapor-particle sampler containing an improved annular denuder which allows both vapor and particulate phase organic species to be recovered and quantified.

It is another object of the invention to provide an integrated organic vapor-particle sampler whose parts can be used in several different configurations, depending on the purpose of its use.

It is another aspect of the invention to provide a semi-volatile organic reversible gas sorbent for use in an integrated diffusion vapor-particle sampler comprising macroreticular resin agglomerates of randomly packed microspheres with the continuous porous structure of particles ranging in size between 0.05–10 $\mu$m.

It is still another object of the invention to provide a sorbent coating which will not release particles when air flows over or through the coated air sampling device.

It is yet another object of the invention to provide a sorbent coating which does not use adhesives which could dissolve in solvent washes of the coated surface.

It is still yet another object of the invention to provide a process for sampling semi-volatile organic compounds using the improved integrated vapor-particle sampler.

It is another object of the invention to provide a process for coating a denuder which minimizes displacement of the absorbent during transport, collection, and subsequent extraction for analysis.

It is still another object of the invention to provide a process for extraction of organic species from the coating of the annular denuder.

DEFINITIONS

Figure 1:
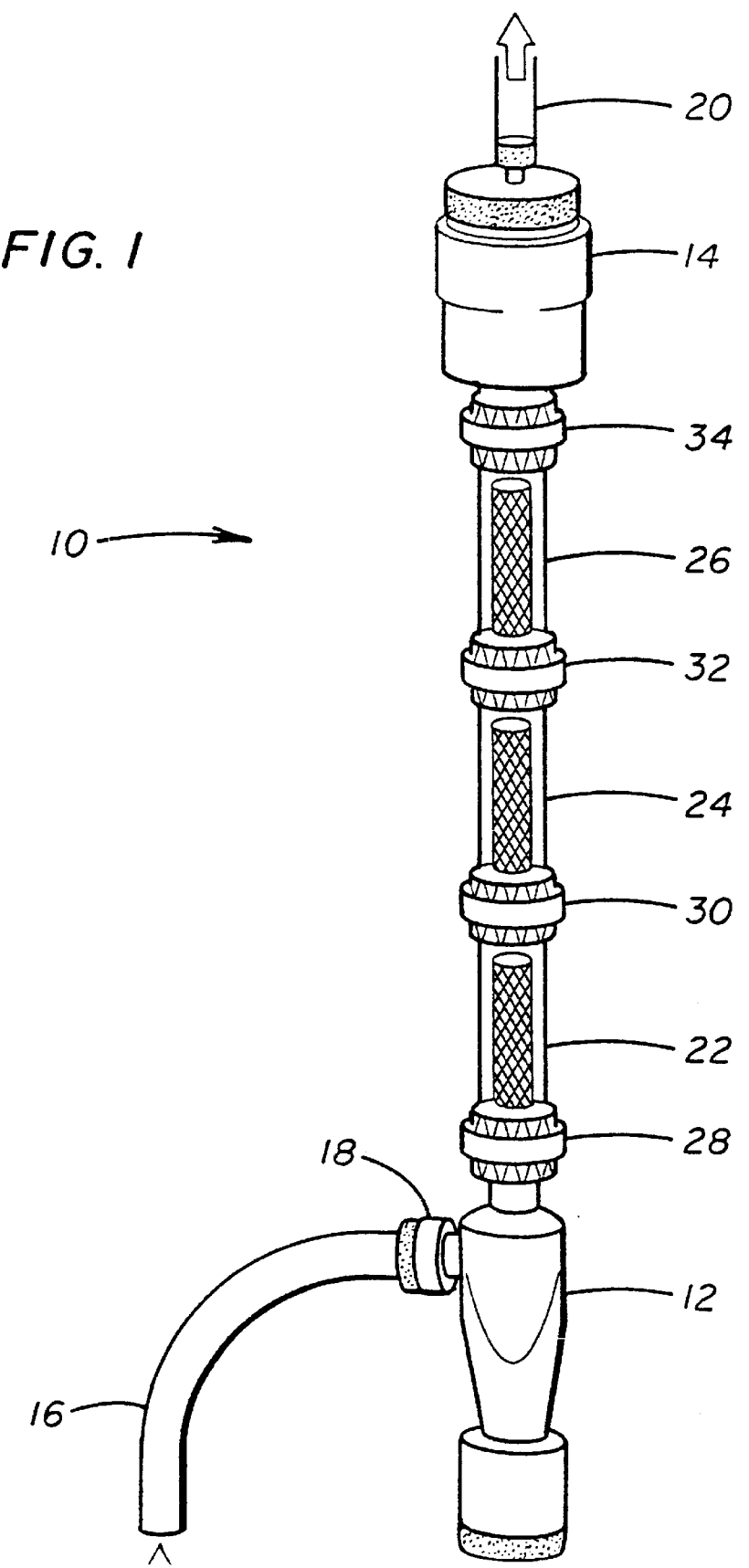
FIG. 1 is a side view of the integrated vapor-particle sampler of the invention with portions cut away, where three denuders are placed in front of the filter pack.

As used herein:

"Integrated organic vapor-particle sampler (IOVPS)" means an apparatus able to quantitatively sample and separate semi-volatile organic gases and particulate components.

"Macroreticular" means the unique structure of the polymers used in the present invention which are produced by a phase separation technique utilizing a precipitating agent.

"Microporosity" or "microreticularity" means molecular porosity presently known in the art as essentially homogenous crosslinked gels wherein the pore structure is defined by molecular-sized openings between polymer chains.

"Macroreticular resins" means resins which contain significant non-gel porosity in addition to the normal gel porosity, where the non-gel pores have been seen, by electron micrographs, to be channels between agglomerates of minute spherical gel particles, the prior art gel resin having a continuous polymeric phase while the macroreticular resin having agglomerates of randomly packed microspheres with a continuous non-gel porous structure.

"Porous" as used herein refers to the channels or openings between agglomerates of minute spherical particles.

DETAILED DESCRIPTION OF THE INVENTION

The present invention concerns a quantitative organic vapor-particle sampler which can efficiently sample both semi-volatile organic gases and particulate components through the use of a unique sorbent resin coating.

The invention further concerns a semi-volatile organic reversible gas sorbent for use in an integrated diffusion vapor-particle sampler comprising macroreticular resin agglomerates of random packed microspheres with the continuous porous structure of particles ranging in size between 0.05–10 μm.

In addition to the resin coating, the invention concerns a process for sampling organic vapor/particle gas streams using the sampler of the invention.

I. Integrated Organic Vapor Particle Samplers

A. Description of the Integrated Organic-Vapor Particle Sampler of the Instant Invention The present invention involves a quantitative integrated organic vapor-particle sampler (IOVPS) comprising a new resin-coated annular denuder and filter, which enable organic vapor/particle compositions to be efficiently phase separated and quantitatively measured using a unique sorbent resin coating.

The sampler of the present invention comprises in its broadest aspect a tubular device having an inlet at one end through which organic vapor and particles are introduced, an outlet at the other end through which gases exit, at least one annular denuder interposed therebetween which is coated on the inside surfaces of the annulus with a specially prepared resin absorbent which selectively absorbs organic vapors contained in the gases introduced into the inlet, and a filter which traps and collects the particulate components.

The IOVPS of the present invention are designed to directly measure semi-volatile organic species in both the gas-phase and particle-phase. Since lung deposition patterns of polycyclic aromatic hydrocarbons (PAH) depend on the distribution of PAH between the gas and particle phases, accurate measurements of phase distributions of PAH are needed in order to assess exposure to carcinogenic compounds.

The IOVPS of the invention and its various individual components are seen in FIGS. 1–5. FIG. 1 shows one embodiment of the sampler of the present invention.

As shown in FIG. 1, the integrated organic vapor-particle sampler 10 of this invention comprises an elongated tubular device vertically positioned having attached a cyclone component 12 at the lower end and a filter pack component 14 at the opposite and upper end. An inlet pipe component 16 is joined to the cyclone 12 by means of a coupler 18. An outlet tube 20 projects upward from the filter pack 14.

Positioned intermediate between the cyclone 12 and the filter pack 14 is a plurality of annular denuders 22, 24 and 26 connected to each other, and also to the cyclone 12 and to the filter pack 14 by means of connectors 28, 30, 32, and 34.

The cyclone 12 has an interior baffle arrangement 13 that allows large particles of particulate matter to fall to the floor while gaseous components rise upward when the gas/particulate mixture enters the cyclone through the inlet pipe 16.

The filter pack component 14 comprises an annular support which holds a glass fiber or other type of filter mounted there.

The individual annular denuders 22, 24 and 26 connect to the connectors 28, 30, 32 and 34 by means of threads on the ends of the denuders (not shown) engaging complementary threads on the connectors (not shown). Annuli of the denuders is coated with a resin.

Figure 2:
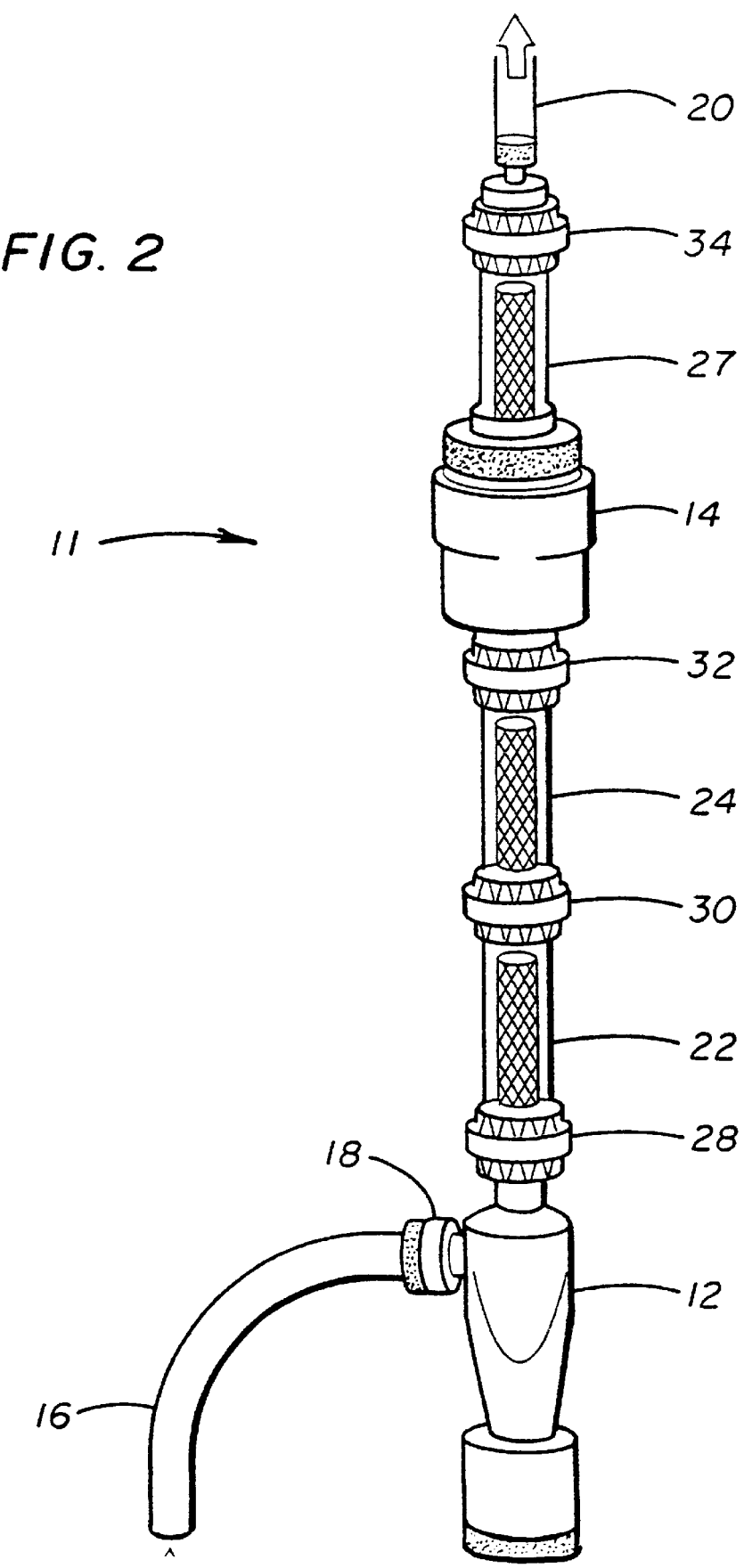
FIG. 2 is a side view of an alternate embodiment of the integrated vapor-particle sampler of the invention, with portions cut away, where two denuders are placed in front of the filter pack and one denuder is placed after the filter pack.
Figure 3:
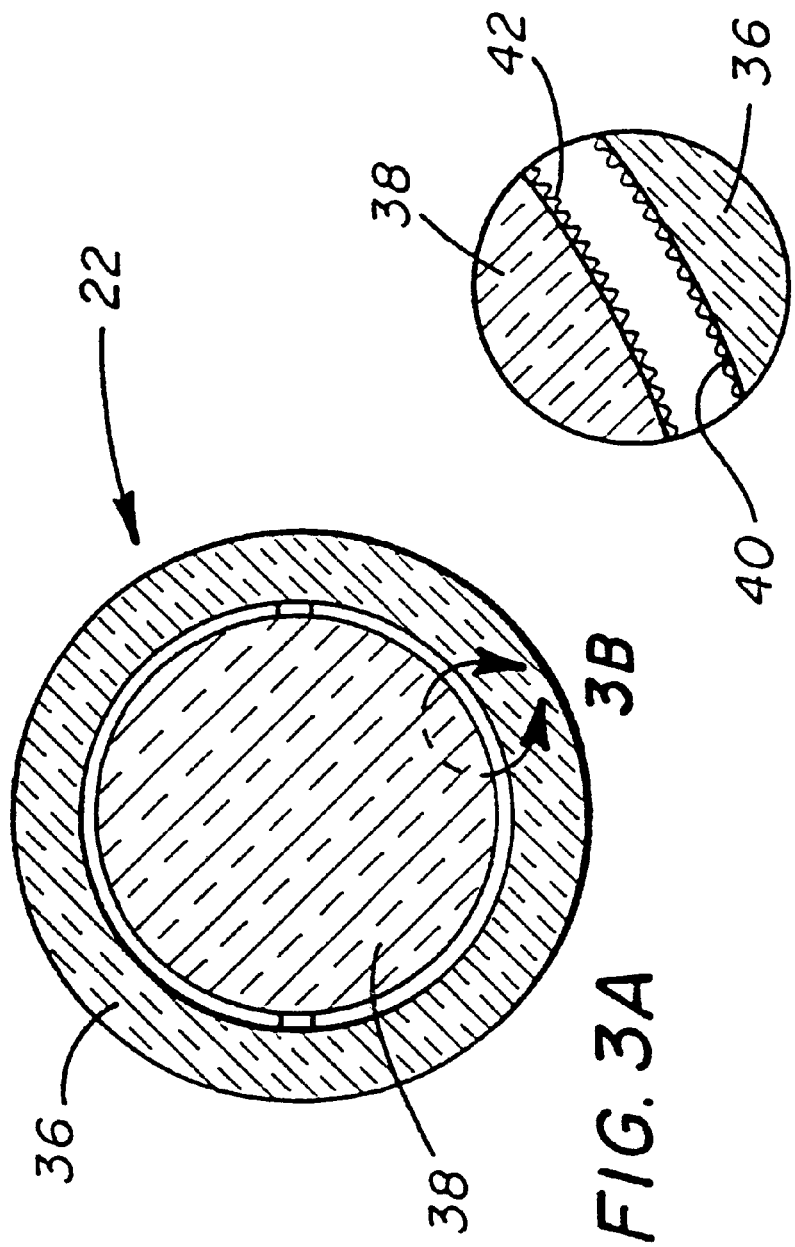
FIG. 3A is a cross-sectional view of a coated single-channel annular denuder.
FIG. 3B represents a section of the denuder seen in FIG. 3A.

FIG. 2 shows an alternate embodiment of the integrated organic vapor-particle sampler of FIG. 1.

The elongated tubular device 11 comprises two denuders 22 and 24, placed between the cyclone 12 and the filter pack 14 and one additional denuder 27, placed between the filter pack 14 and the outlet tube 20.

The annular denuders 22, 24 and 27 are connected to each other, to the cyclone 12, the filter pack 14, and the outlet tube 20, by means of connectors 28, 30, 32 and 34 by means of threads on the ends the denuders (not shown) engaging complementary threads on the connectors, cyclone 12, filter pack 14 and outlet tube 20 (not shown).

The annular denuder sections, shown as 22, 24, 26 and 27 in FIGS. 1 and 2, are coated with ground sorbent particles. The ground sorbent particles adsorb gases from the airstream. The filter pack is a holder for one or more glass or quartz fabric filters which sieve the airborne particles from the airstream. Couplers and fittings are used to connect the components.

FIG. 3A is a cross-sectional view of a coated single-channel annular denuder. FIG. 3B represents a section of the denuder seen in FIG. 3A.

As shown in FIG. 3A, the annular denuder 22 comprises an outer hollow cylindrical tube 36 and an inner cylindrical rod 38, the two rods having the same central axis, and the outer hollow cylindrical tube 36 being concentric with respect to the inner cylindrical tube 38.

The inner cylindrical rod 38 is inset 25 mm from one end of the outer cylindrical tube 36. This end is called the flow straightener end. The other end of the inner cylindrical tube 38 is flush with the other end of the outer cylindrical tube 36. Both ends of the inner cylindrical tube 38 are sealed.

The inner surface 40 of the outer hollow cylindrical tube 36 and the outer surface 42 of the inner cylindrical tube 38 define an annulus therebetween, of which surfaces are coated with a macroreticular resin of the invention described below, and through which annulus the organic vapor/particulate composition passes.

The tubes are connected to each other with small epoxy resin spacers placed at each end of the tubes. The epoxy resin spacers separate the tubes, enabling the annulus to be defined therebetween.

The actual physical components of the denuder can be purchased commercially from University Research Glassware, 118 E. Main St. Carrboro, N.C. 27510. The improved sampler of this invention lies in the particular resin applied to the inside surfaces of the denuder component.

B. Preferred and Alternate Embodiments

One alternate embodiment of the invention, for example, places a denuder or a sorben; bed after the filter pack to collect and measure blow-off from the particles caught on the filters. This embodiment of the integrated organic vapor-particle sampler is shown in FIG. 2.

In the most preferred embodiment of the invention the integrated organic vapor-particle sampler (IOVPS), the denuder is formed of two concentric tubes 36 and 38 which define an annulus therebetween.

Figure 4:
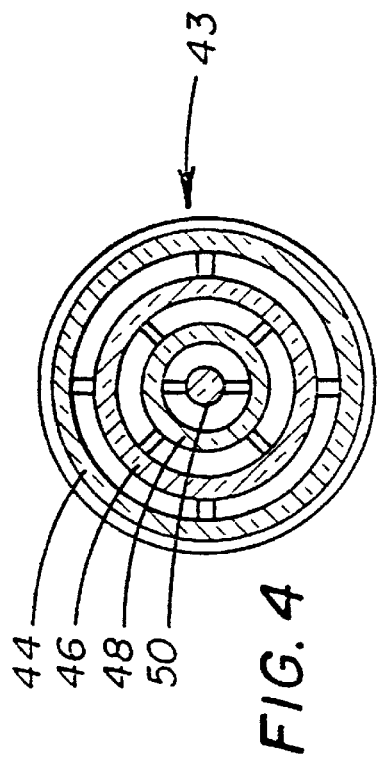
FIG. 4 is a cross-sectional view of a multi-channel annular denuder.
Figure 5:
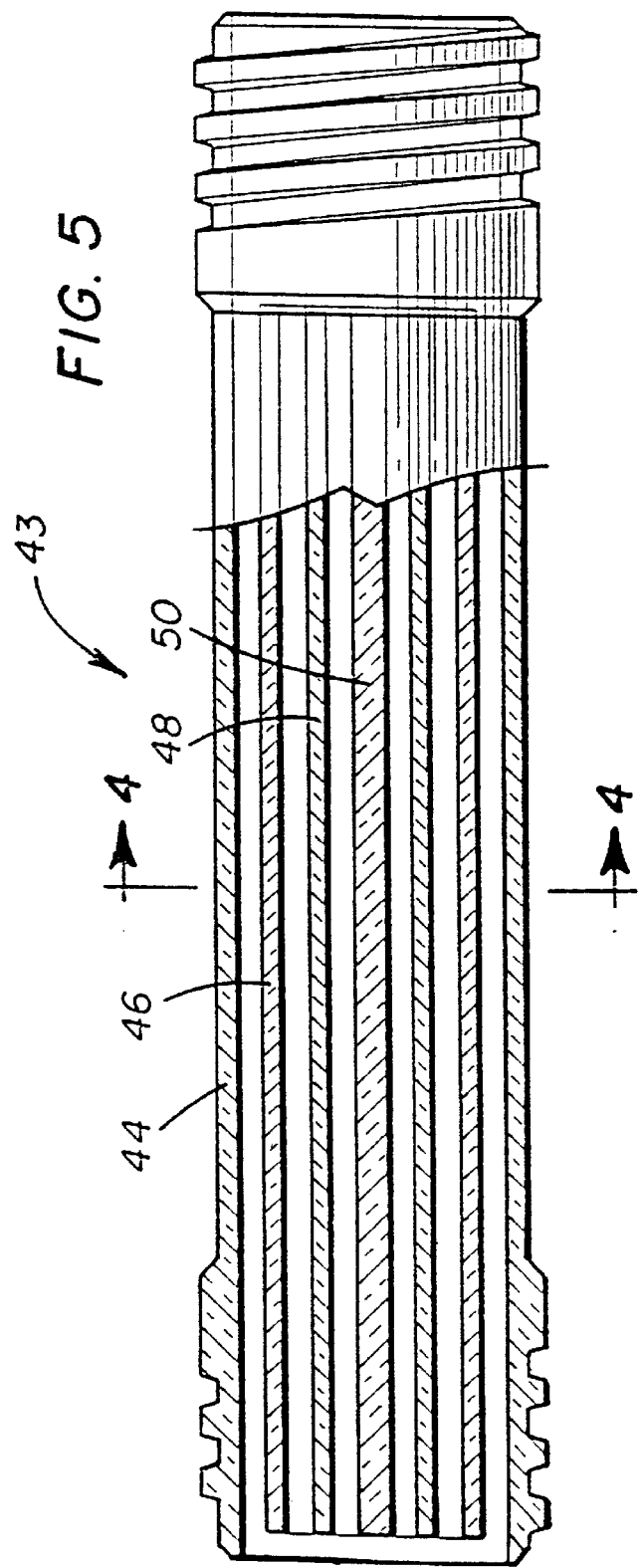
FIG. 5 is a plan view of a multi-channel annular denuder.

Yet another embodiment of the invention utilizes three or more concentric tubes with an annulus defined between each pair of adjacent concentric tubes. A cross section of such a multi-channel denuder consisting of four concentric glass tubes is shown in FIG. 4. FIG. 4 is the cross-sectional view of a multi-channel denuder 43 consisting of four concentric glass tubes 44, 46, 48, 50. FIG. 5 shows (partially in section) the multi-channel denuder 43 of FIG. 4 in side view.

In still another embodiment of the invention the annulus of the annular denuder is lined with polyurethane foam.

Still another embodiment of the IOVPS combines the coating of the IOVPS with structural elements of Gas and Particle (GAP) samplers which are similar in design to the IOVPS, but have thirty times the surface area. The Gas and Particle samplers were designed for operation as difference denuders for measurement of the phase distributions of pesticides in outdoor air.

The IOVPS of the invention has been developed to use hardware that has already been validated for sampling of acid gases. The sampler geometry and flow characteristics have been thoroughly investigated. The advantages of sampling gas phase pollutants with annular diffusion denuders have now been extended to organic species that are adsorbed by the macroreticular resin XAD-4 and similar adsorbents.

The modular design of the IOVPS allows the configuration of its components to be tailored for the needs of each investigation. For example, the total length of the denuder section can be adjusted by choice of the number of denuders used, and different coating types could be used in the different pre-filter sections. The filter holder can contain up to four filters if desired. The post-denuder section can be a denuder, sorbent bed or polyurethane foam collector.

From the foregoing, one skilled in the art can recognize that the present invention provides a new instrument for the quantitation of gas-phase and particle-phase species of semi-volatile organic compounds. The foregoing disclosures and descriptions of the invention are illustrative and explanatory of the invention. Without further elaboration, it is believed that one of ordinary skill in the art can, using the preceding description, utilize the present invention to its fullest extent.

Additional embodiments will be obvious to those skilled in the art of the present invention. Various materials may be used which meet the requirement of macroporosity discussed herein. A variety of denuder geometries may also be used which are functionally equivalent to the denuder geometry illustrated herein. Alternative methods of preparing the denuder with the advantageous coating described below may be used.

The IOVPS represents a significant improvement on conventional filter-sorbent bed samplers designed to sample gas-phase semi-volatile organic compounds. It addresses the conventional samplers' inherent problems, which include positive and negative artifacts and the inability to quantitatively recover gas-phase species. The IOVPS strips the gas-phase species from the air stream before particle collection by a filter. Although volatilization losses of semi-volatile species from particles are possible if the IOVPS is operated at a high face velocity, the IOVPS can be configured to correct for "blow-off" from the filters, by placing a denuder or sorbent bed downstream of the filter.

C. Assembly of the Integrated Organic Vapor-Particle Sampler (IOVPS)

The IOVPS has three primary elements: a size-selective inlet, annular denuder sections, and a filter pack for one or more filters.

These components are shown in FIGS. 1 and 2 described in detail above.

The size-selective inlet, a Teflon-coated aluminum cyclone, whose function is to provide a 90°bend and orifice for separation of particles greater than 2.5 $\mu$m diameter from the sampled airstream was selected. An impaction plate could also have been used, although the cyclone design is preferred for accurate separation of large particles from the airstream without contaminating the airstream with the grease which an impactor plate requires.

A selected plurality of annular denuder sections was coated with the ground sorbent particles as described below. The coating adsorbs gases from the airstream. After coating, the denuder sections were attached to the cyclone and each other by means of connectors.

A filter pack containing one or more glass or quartz fabric filters which sieve the airborne particles from the airstream was then connected to the last denuder by means of a connector.

Optionally, another ground sorbent coated denuder section may be added after the filter pack to collect any filter "blow-off" gases.

D. Samplers Used for Field Testing

The sampling configuration of IOVPS which was used for the field testing is seen in FIG. 1. commercially available single channel glass denuders, 22 cm long, from University Research Glassware, Carrboro, N.C. were used with a Teflon-lined aluminum cyclone preceding the first denuder. The cyclone was designed to remove particles with an aerodynamic diameter of less than 2.5 micrometers. Three denuders were connected in series between the cyclone and a Teflon filter pack. Pre-extracted and pre-weighed Teflon-coated glass fiber filters were used. The sorbent bed sampler used an aluminum open-face filter holder with Teflon-coated glass fiber filters followed by a glass tube packed with 2.5 g cleaned XAD-4 resin. Flow rates were measured with a dry gas test meter. This configuration was used to evaluate breakthrough and capacity as functions of flow rate and sampling time. The IOVPS sampled indoor laboratory room air in these experiments. As the emphasis was on evaluation of its collection of gas-phase components, no sorbent or denuder was usually used downstream of the filter.

The configuration used to sample environmental tobacco smoke (ETS) is seen in FIG. 2. Two denuders were used between the cyclone and filter pack, the third denuder followed the filter pack. Two filters were used in the filter pack when sampling ETS. In one experiment this configuration was also used to sample laboratory air. In this configuration the whole phase distribution could be determined since correction could be made for adsorption characteristics of the filter and for evaporation from particles.

II. Coating Resin and Its Preparation

One critical aspect of this invention is the inventive macroreticular resin which is used to coat the annulus of the denuder of the integrated organic vapor-particle sampler of the instant invention.

A. Resin Materials

It has been found that gas phase polycyclic aromatic hydrocarbons (PAH) can be separated most efficiently from particulate matter and quantitative measurements made by using a macroreticular resin, such as described in U.S. Pat. No. 4,224,415, incorporated by reference.

The macroreticular resin is the unique structure of the polymers used in the present invention which are produced by a phase separation technique utilizing a precipitating agent. While conventional prior art resins are essentially homogeneous crosslinked gels where the only pore structure is defined by molecular-sized openings, also called microporosity or microreticularity, between polymer chains, macroreticular resins, by contract, contain significant non-gel porosity in addition to the normal gel porosity.

Figure 6:
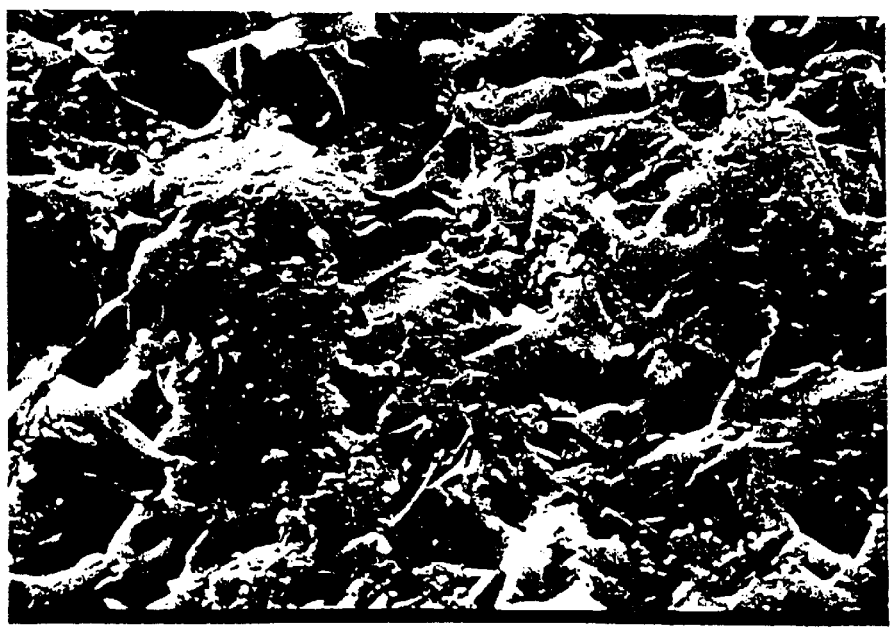
FIG. 6 is a photo-micrograph showing the surface of an sandblasted uncoated glass denuder.
Figure 7:
FIG. 7 is a photo-micrograph showing the surface of a sandblasted resin coated denuder of the invention.
Figure 8A:
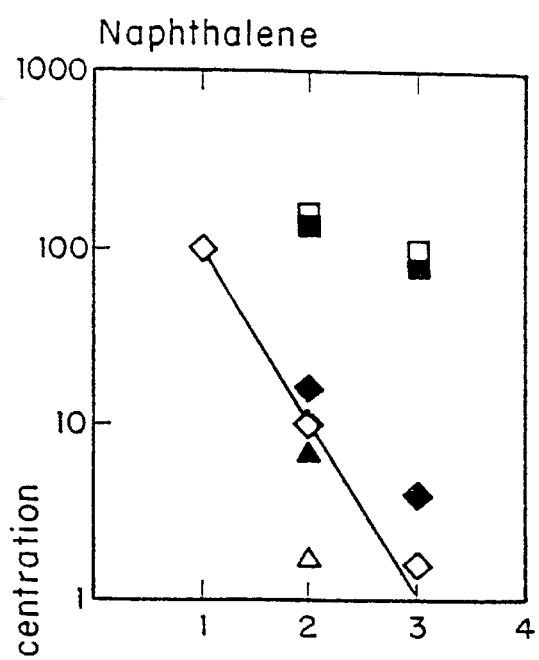
FIG. 8 shows semi-logarithmic plots of napthalene (FIG. 8A), 1-methylnaphtalene (FIG. 8B), fluorene (FIG. 8C) and phenanthrene (FIG. 8D) gas-phase PAH as a function of denuder position for various flow rates and two sampling times.
Figure 8B:
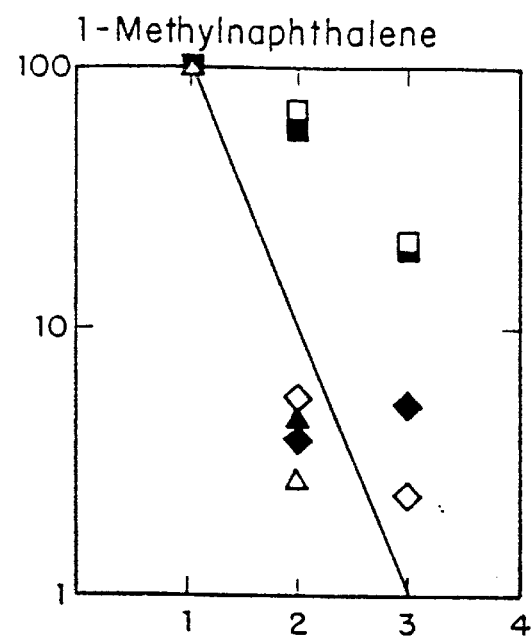
Figure 8C:
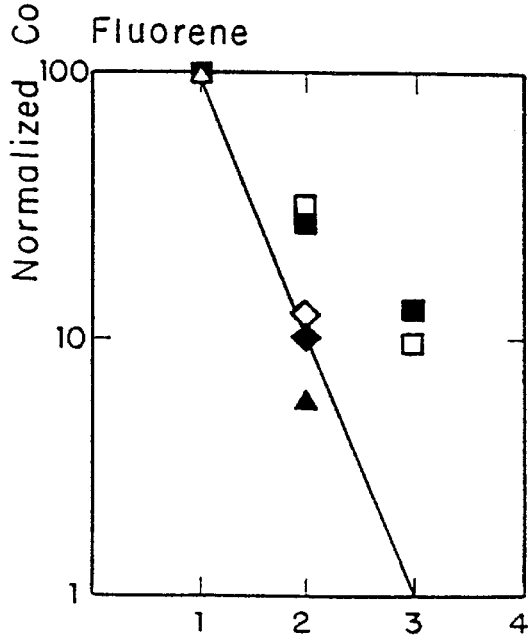
Figure 8D:
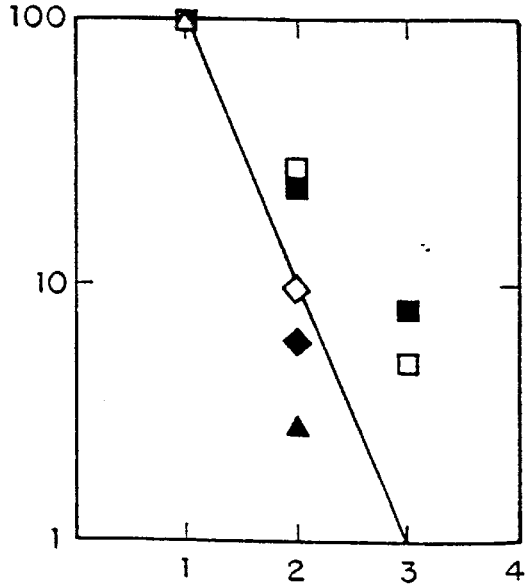
Figure 9A:
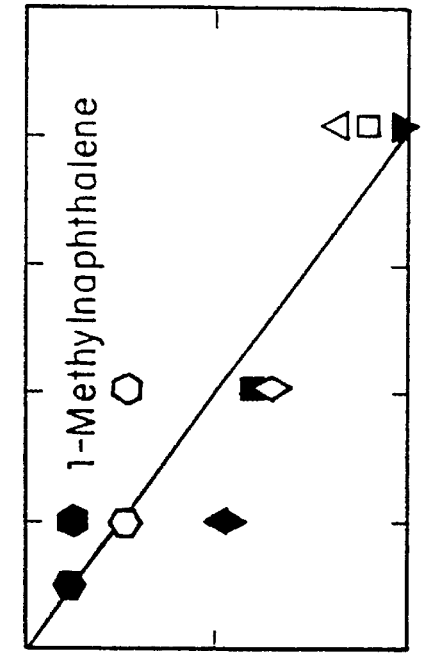
FIG. 9 shows semi-logarithmic plots of outlet concentration to inlet concentration of napthalene (FIG. 9A), 1-methylnapthalene (FIG. 9B), fluorene (FIG. 9C) and phenanthrene (FIG. 9D), gas-phase PAH concentrations as a function of length of denuder to volume of sampled air for various flow rates and two sampling times.
Figure 9B:
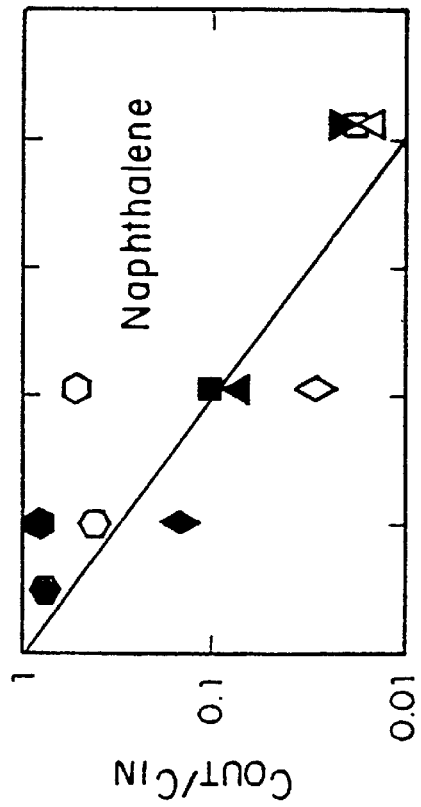
Figure 9C:
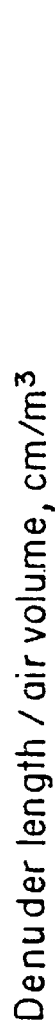
Figure 9D:
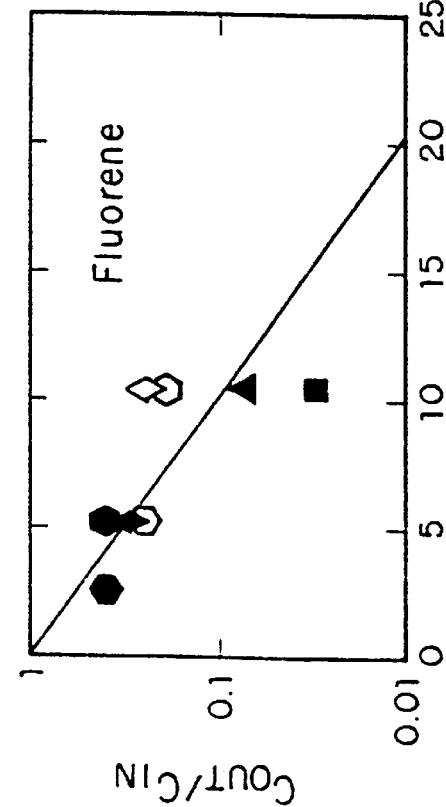

The non-gel pores have been seen by electron-micrographs to be channels between agglomerates of minute spherical gel particles. The macroreticular resin of the invention is seen in FIG. 7. FIG. 6 is a photo-micrograph showing the surface of a sandblasted uncoated glass denuder. FIG. 7 is a photo-micrograph showing the surface of the sandblasted denuder coated with macroreticular resin of the invention.

The prior art gel resin has a continuous polymeric phase while the macroreticular resin is clearly shown to be agglomerates of randomly packed microspheres with the continuous non-gel porous structure. The term porous refers to the channels or openings between agglomerates of minute spherical particles.

The absorbent of the present invention preferentially comprises a macroreticular resin which is applied to the inside surface of the annulus after preparation in the manner described hereinafter.

The most preferred macroreticular resin is a styrene divinyl benzene copolymer, commercially available from Rohm and Haas Corporation, Philadelphia, Pa., under the trade name XAD-4. XAD-4 is a macroreticular cross-linked aromatic polymer with a surface area of 780 m$^2$/g and a porosity volume percentage of 45%. Its pore size ranges from 1–150 Å and its average pore diameter is 50 Å. XAD-4 density is 1.02 g/mL.

Other suitable resins of the same family include those sold under the trade names XAD-2, XAD-16, Chromosorb 102, and Ostion SP-1. These, and other macroreticular resins suitable for use in the annular denuders, are set forth in Table 1.

TABLE 1

Macroreticular Resins Suitable for Use with the IOVPS

| Common Name | Type | Area (m$^2$g) | Pore Size (Å) |
|---|---|---|---|
| XAD-1 | styrene-divinylbenzene (DVB) | 100 | 200 |
| XAD-2 | styrene-divinylbenzene (DVB) | 350 | 90 |
| XAD-4 | styrene-divinylbenzene (DVB) | 780 | 50 |
| Ostion SP-1 | styrene-divinylbenzene (DVB) | 350 | 85 |
| Chromosorb 102 | styrene-divinylbenzene (DVB) | 350 | 90 |
| Chromosorb 105 | polyaromatic polystyrene | 650 | 500 |
| Chromosorb 106 | polyaromatic polysterene | 750 | — |
| Synachrom | ethylvinylbenzene - DVB | 570 | 45 |
| Porapak Q | ethylvinylbenzene - DVB | 735 | — |
| XAD-7 | methylmethacrylate | 450 | 80 |
| XAD-8 | methylmethacrylate | 140 | 250 |
| Spheron MD | methacrylate - DVB | 320 | — |
| Spheron SE | methacrylate-styrene | 70 | — |
| Tenax - TA | 2,6-diphenyl-p-phenylene oxide | 35 | 2000 |

Still other materials which can be used to coat the annulus of the denuders include non-bonded silica, bonded silica, alumina, fluoracil, activated carbons and carbon black, and a porous polymer resin available from many different sources, known under the trade name Tenax-TA. Tenax-TA, a 2,6-diphenyl-p-phenylene oxide resin, has a surface area of 35 m$^2$/g, an average pore size of 200 nanometers, and a density of 0.16 g/cc. Its properties are described in the Alltech Chromatography catalog 300, page 157 (1993), incorporated herein by reference. Tenax-TA may be obtained from Alltech Associates, Inc., 2051 Waukegan Road, Deerfield, Ill. 60015.

As stated above, the most preferred resin for coating of the surface of the annulus is XAD-4. This is a styrene-divinyl benzene resin having an area of 780 m$^2$/g and an average pore diameter of 50 Å.

Insofar as applicable for preparation of macroreticular resin of the invention, certain techniques described in and the U.S. Pat. No. 5,302,191 itself are hereby incorporated by reference.

B. Preparation of the Coating

The coating material was ground into fine particles before application to the sampling equipment. About 8 grams of macroreticular resin beads such as XAD-4, XAD-7, XAD-16, Tenax-GC, and various ion exchange beads, activated carbon particles such as Carbotrap and chromatographic-grade silica were ground separately using a commercial centrifugal grinder. The grinder, a Fritsch Pulverisette, type 05.101, with an agate container and agate balls, operated at speed 7 of 10, for between 6 and 21 hours. The best grinding time depended on the nature of the particles. The aim was reduction of average particle size to less than 1 micrometer. XAD-4 which had been ground for six hours contained a few beads of unground resin which were removed from the batch before further processing. It was also possible to obtain suitable particles by using a hand-operated mortar and pestle to grind macroreticular resins. The finely-ground particles were separated from the remainder of the batch by forcing the mortar output through a several layers of fine stainless steel mesh.

C. Removal of Impurities and Very Fine Particles

The ground resin or other sorbent was extensively cleaned by solvent extraction to remove impurities which, if not removed before air sampling, interfered with subsequent quantitative analysis of adsorbed species. After grinding, the particles were sonicated with 200 mL cyclohexane for 20 min. Aliquots (5 mL) of the suspension were transferred to a vacuum filtration device loaded with an unlaminated Teflon filter with nominal pore size of 0.5 micrometers and outer diameter 47 mm (Millipore Corp., FHUP 0047). Vacuum was applied until the sorbent was almost dry, and then another aliquot of suspension was transferred to the same device. The transfer and filtration were repeated until half the slurry was transferred. Methanol was added in two 25 mL aliquots. Vacuum was applied until the sorbent was dry enough to crack. The filtration barrel was carefully removed, exposing the Teflon filter and cleaned sorbent which were then removed to a clean watch glass for air drying. The remainder of the cyclohexane slurry was treated in the same way. Acceptable blank levels of the analytes of interest were found. Besides collecting the cleaned sorbent, the filtration process removed sorbent particles smaller than the pore size of the filter which otherwise clogged capillary tubing in the analytical instrumentation whose use is described below. After the clean ground sorbent particles were dry they were carefully scraped off the filter into a glass mortar and ground by hand for about one minute before storage in a stoppered glass bottle.

D. Properties of Resin Beads

The coating material is ground into fine particles before application to the sampling equipment. Macroreticular resin beads and various ion exchange beads, activated carbon particles such as Carbotrap and chromatographic-grade silica are ground separately using a commercial centrifugal grinder. The goal of the grinding is reduction of the average particle size to less than 1 $\mu$m. Remaining unground resin is removed from the batch before further processing. It is also possible to obtain suitable particles by using a hand-operated mortar and pestle to grind macroreticular resins. The finely-ground particles are separated from the remainder of the batch by forcing the mortar output through several layers of fine stainless steel mesh.

Previously, when the diameters of a few unground XAD-4 particles were measured using an optical microscope, typical diameter of the particle was 0.76 mm. When a larger sample was measured by placing ten beads end to end along a machinist's scale and noting the length, the average diameter was 0.95 mm.

The unground beads of the commercially available resins are almost as large in diameter as the annular space of the IOVPS (1 mm) and would cause complete blockage of the annulus because both surfaces need to be coated. For denuders of larger annulus (up to 3 mm in the higher capacity IOVPS), the annulus would be reduced to 1 mm and the presence of such a bumpy coating would induce turbulence in the gas flow. Turbulence would lead to particle deposition and the phase distribution measurements would be impossible to achieve.

Additionally, unground beads do not form a slurry, but adhere temporarily to a glass surfaces rod as long as the beads are wet with a compatible solvent such as hexane. They fall off as the solvent evaporates. The behavior is similar for attachment to sandblasted surfaces. Such large particles cannot be used as a denuder coating because their ability to adhere is exceeded by their mass. Properties of ground and unground XAD resin particles are seen in Table 2.

Table 2 below shows the surface area and volume calculations for unground and ground particles and the effect of grinding on surface area of a slurry.

TABLE 2

Surface Area and Volume Calculations for Ground and Unground XAD Resin

|  | Diameter $\mu$m | Diameter cm | Radius cm | Surface Area cm$^2$ $4\pi r^2$ | Volume cm$^3$ $(4/3)\pi r^3$ | Surface Area/Volume cm$^{-1}$ | Ratio ground/unground |
|---|---|---|---|---|---|---|---|
| unground | 764 | 0.0764 | 0.0382 | 0.018337 | 0.000233 | 78.53 | |
| ground | 0.753 | 7.53E−05 | 3.77E−05 | 1.78E−08 | 2.24E−13 | 79681 | 1015 |

|  | Diameter $\mu$m | Diameter m | Radius m | Surface Area m$^2$ | Volume m$^3$ | Surface Area/Volume m$^{-1}$ | Ratio ground/unground |
|---|---|---|---|---|---|---|---|
| unground | 764 | 0.000764 | 0.000382 | 1.83E−06 | 2.33E−10 | 7853 | |
| ground | 0.753 | 7.53E−07 | 3.77E−07 | 1.78E−12 | 2.24E−19 | 7968127 | 1015 |

The ground resin or other sorbent must be cleaned by solvent extraction to remove impurities which, if not removed before air sampling, interfere with subsequent quantitative analysis of adsorbed species. The particles are then sonicated and dried in a vacuum filtration device loaded with a filter with nominal pore size of 0.5 $\mu$m. Methanol is added and vacuum reapplied until the sorbent is dry enough to crack. The clean sorbent is then removed to a clean watch glass for air drying.

This filtration process removes sorbent particles smaller than the pore size of the filter which otherwise clogs capillary tubing in the analytical instrumentation.

The clean dry ground sorbent particles are next carefully scraped off the filter into a glass mortar and ground by hand for about one minute and then stored for future use.

E. Electron Microscopy

The coated and uncoated glass fragments were analyzed at the U.S. Environmental Protection Agency Scanning Electron Microscope Laboratory in Research Triangle Park, North Carolina. The instrument was an Amray Model 1000 scanning electron microscope, an analog instrument with manual stage control and resolution of about 70 nm at 30 keV. The instrument was used at 20 keV, 50 $\mu$Å beam, 26° tilt and 12 mm working distance. The samples were scanned at 500 and 2000 times magnification. Analysis of the particle size distribution of the XAD-4-coated fragment found that the coating was composed of particles with median and average diameters of 0.7 and 0.9 $\mu$m, respectively. The geometric mean was 0.75 $\mu$m, with a geometric standard deviation of 1.8 $\mu$m. The uncoated and coated annular denuder surfaces, respectively, are seen in FIGS. 6 and 7.

For testing, an annular denuder section (manufactured by URG) was taken from the laboratory's stockpile at random and intentionally shattered. Two small fragments were selected for electron microscopic analysis. One 3 mm×3 mm fragment was coated by adding the fragment to 2 mL of a slurry of ground XAD-4 (30 mg in 200 mL hexane) and ultrasonicating for 5 minutes. The fragment was removed with tweezers and dried on a clean microscope slide in a nitrogen atmosphere for 5 minutes. The process was repeated for a total of four times. After the last coating, the surface had a visible thin coating of white powder which was not dislodged when the fragment was tapped gently. A similar uncoated fragment from the same denuder was also selected for electron microscopy.

III. Coating of Integrated Organic Vapor-particle Sampler

A. Techniques Used for Denuder Coating

Typically, a sandblasted glass annular denuder section is capped at one end, filled with spectral grade acetonitrile, capped at the other end, and cleaned by sonication. An ultrasonic bath large enough to accommodate the whole length of the section is used. The cleaned section is dried by passing a low flow of clean nitrogen gas through it for a few minutes. The total mass of the clean uncapped denuder section is determined.

Slurries of the macroreticular resin are applied to the denuder. First, the slurry is sonicated briefly to assure suspension of the resin in hexane as some settling of the slurry may occur during storage. The denuder is then capped at one end and the slurry is poured into the denuder. The other end of the denuder is capped and the denuder manually inverted about 10 times. The remaining slurry is drained from the denuder into a beaker. The denuder is dried with a low flow of clean nitrogen for 30 to 60 seconds. The coated denuder is weighed again.

The coating, drying and weighing procedure of the denuder is repeated at least ten times. After coating of the denuder is complete, hexane is poured into the capped denuder which is then inverted a few times. The hexane is drained out.

The glued areas of the glass in the denuder ends are sonicated in hexane to remove any loose resin which might otherwise be blown off the glue surface during sampling.

The net coating mass is determined by weighing the coated denuder section after the hexane rinse.

The coating technique produces a stable even coating which remains in place during sampling even at 20 L/min for 24 hours. However, the caps and connectors must be free of XAD-4 powder before they are attached to the coated denuders. Dry powder from the caps or connectors may lead to deposits of XAD-4 on the afterfilter. This would lead to erroneous results.

Sandblasted glass surfaces of any geometry can be coated by adapting the technique described above. For example, the suspended slurry of sorbent in solvent can be poured over a flat surface; a tube can be filled with the slurry, or the slurry can be poured through while the tube is rotated by hand or motor. A rod can be dipped into the slurry while it is suspended in a beaker or graduated cylinder.

The integrated organic vapor-particle samplers are inserted in the chamber to be tested. The ventilation ducts and chamber doors are sealed shut with duct tape during the experiment to minimize the air exchange rate and improve the accuracy of the results of the analysis.

The integrated organic vapor-samplers are then removed in sequence.

For studies performed in development of this invention, sandblasted glass annular denuder sections 22, 24 and 26, seen in FIG. 1, were purchased from University Research Glass, Carrboro, N.C., part number URG 2000-30B, 220 mm length. They were capped at one end with Teflon-lined caps, filled with spectral grade acetonitrile, capped at the other end, and cleaned by sonication for 20 minutes. An ultrasonic bath large enough to accommodate the whole length of a section was used. The cleaned sections were dried by passing a low flow of clean nitrogen gas through them for a few minutes. The total mass of the clean uncapped denuder was determined using a Mettler balance, Model H35AR (to 0.0001 g). Slurries of density 50, 100, 200 and 250 mg ground XAD-4 in 30 mL hexane were prepared and used to test the coating procedure.

Each slurry was applied in the same way. First, the slurry was sonicated briefly to assure suspension of the resin in hexane. Some settling of the XAD-4 was observed for a slurry density of 250 mg/30 mL hexane. Then the slurry was poured into the denuder which had been capped at one end. Then the other end was capped and the denuder manually inverted about 10 times. The remaining slurry was drained into a beaker from the denuder.

The denuder was dried with a low flow of clean nitrogen for 30 to 60 sec. The coated denuder was weighed again. The coating, drying and weighing procedure was repeated at least ten times. After coating was complete, hexane was poured into the capped denuder which was then inverted a few times. The hexane was drained out, and each end was sonicated in hexane just covering the glued areas of the glass. The hexane rinse removed any loose XAD-4 which might otherwise be blown off the glass surface during sampling. The net coating mass was determined by weighing the coated section after the hexane rinse.

The results showed that the greater the slurry density, the more quickly the denuder gained mass, but the maximum coating remained the same regardless of the slurry density. Use of slurries of greater than 500 mg/30 mL hexane led to streaky coating. However, the net coating mass was typically 10–20 mg. for clean single-annulus denuder sections of 22 cm length which had previously been stripped of the XAD-4 by sonication in acetonitrile. Ethyl acetate removed XAD-4 even more thoroughly than acetonitrile. The net coating mass was reproducible to +1 mg for individual denuders. Based on the results described, a slurry density of 200 mg/30 mL hexane was chosen for routine coating procedures.

B. Preparation of Multi-channel Annular Denuders

The IOVPS may have one, but has preferably multiplicity of denuders.

The coating technique was applied to 5-channel annular denuder sections (URG-2000-30x; sandblasted length 125 and 220 mm) whose interior surfaces had been sandblasted in the same manner as the single channel denuder sections. When ground XAD-4 was used as the sorbent, the net coating mass was about three times that found for a single-channel denuder of the same coated length. That result is consistent with the measured difference in surface area between the single and five-channel annular denuder sections of similar sandblasted lengths.

C. High Capacity IOVPS

Gas and Particle (GAP) samplers are similar in design to the IOVPS, but the GAP samplers have thirty times the surface area. They were designed for operation as difference denuders for measurement of the phase distributions of pesticides in outdoor air.

An embodiment of the IOVPS which combines the coating of the IOVPS with structural elements of GAP samplers was prepared as follows. The adsorbent coating, crushed Tenax particles imbedded in silicone gum, was removed from the glass denuder sections of two GAP samplers by rinsing the inside of the denuder section with dichloromethane. The six concentric tubes were disassembled, and sections 55 cm in length were sandblasted on the inside and outside with silicon carbide particles of mesh size 320.

The denuders were next cleaned in acetonitrile and hexane and then coated with ground XAD-4 using procedures based on those described above. The tubes were carefully reinstalled into the outer shell of the GAP denuder. A slurry of 3.2 g ground XAD-4 in 490 mL hexane was sonicated for 10 minutes and poured into the reassembled denuder section after one end had been capped. After capping the other end, the denuder was rotated along its axis and from end to end for ten times in each direction. The slurry was poured out, collected, sonicated again for 5 min, and then the coating step was repeated twice. Following a hexane rinse to remove fine particles, the coated GAP denuder section was dried with a stream of dry nitrogen gas. The caps were reapplied, and the denuder was stored at room temperature until the field test.

D. Coating Versus Sand Grit Size on Coated Glass Disks

Six pre-weighed Pyrex glass discs of 3.9 cm diameter were ground on one side with a range of Carborundum (silicon carbide) particles with grit sizes 80, 150, 240, 320, 400 and 600. After cleaning by sonication with acetonitrile each disc was coated with XAD-4 using a modification of the procedures disclosed in the application. Because the discs were flat, the suspension was poured over three of them as they lay flat, ground side up, in a watch glass before the slurry was sloshed around over the discs ten times for good contact. Each disc was rinsed ten times with hexane to remove unattached particles. Any powder on the smooth back of the disk or edge was removed by wiping before mass determination. The net coating mass and coverage data are presented in Table 3.

TABLE 3

Coating v. Sand Grit Size for Coatings on Selected Glass Discs

| Grit size | Net mass mg | Coverage mg/cm$^2$ | Track width micrometer |
|---|---|---|---|
| 80 | 0.3 | 0.02 | |
| 150 | 0.3 | 0.02 | |
| 240 | 0.1 | 0.01 | 70 |
| 320 | 0.4 | 0.03 | 50 |
| 400 | 0.2 | 0.01 | 40 |
| 600 | 0.3 | 0.02 | 20 |

D. Evaluation of Coating Stability on the Denuders

The coating stability was evaluated from the post-denuder filter in three ways: a) by visual examination, b) by mass determination, and c) by evaluation of the PAH concentration distribution for the particle extract.

After introduction of the final hexane rinse to the coating procedure there was routinely no detectable deposition of XAD-4 on the post-denuder. Filter- and filter loading and extract PAH distribution were similar for filters from both the sorbent and denuder sampling trains. The coating was stable during sampling at flow rates up to 20 L/min, as assessed by visual inspection of black after filters that were used for 24 hours of pump operation. Inspection of Teflon filters that had been used to filter denuder extracts showed that the coating was not removed by static solvent extraction, using two rinses of the intra-annular space, at 45°

C. When observed, deposition of ground XAD on the post-denuder filter during sampling appeared as higher than expected filter mass and higher than expected semi-volatile PAH concentrations in the filter extracts.

IV. Process of Sampling Semi-Volatile Organic Compounds

Apparatus assembly, resin preparation and purification, denuder coatings and sample preparations are as described above or below.

A. Laboratory IOVPS Emulation

The IOVPS was evaluated by sampling indoor laboratory air at room temperature (about 21° C.). The room was free of indoor combustion sources, and therefore the air represented outdoor air that had been brought into the building by the ventilation system. Sampling was done at 5, 10 and 20 L/min for 3 and 6 hours, using three single-channel annular denuders in the configuration 0.075 seconds, respectively. Filter face velocities were 8, 17 and 33 cm/sec, respectively. One experiment was done at 20 L/min for 22 hours. Separate clean components were used for each condition. The exposed denuders were refrigerated before analysis if the extraction could not be carried out immediately. The filters were stored in the freezer before analysis.

Parallel sampling was done using a filter followed by a sorbent bed filled with 2.5 g unground XAD-4 resin beads. The filter-sorbent sampler was similar to that described by Loiselle et at., *Indoor Air,* 2:191–210 (1991), except that the filter holder was stainless steel, and the flow rate was 20 L/min. The XAD-4 resin had been cleaned by sequential Soxhlet extraction in dichloromethane and methanol. After heating in $N_2$ at 40° C. in a fluidized bed for four hours the resin was stored in a sealed bottle until use.

B. Sampling Conditions

The optimal sampling conditions for indoor air without environmental tobacco smoke were chosen by consideration of the data obtained at various flow rates and sampling times. This was done by a) determining the observed concentrations of all detected PAH in each denuder section; b) determining the percentages of naphthalene and its methyl derivatives, fluorene and phenanthrene that were trapped on the first of three denuders; and c) selecting conditions for which the first denuder collected at least 90% of the most volatile species, namely the three naphthalenes. Compounds that are less volatile than the naphthalenes were trapped at greater than 90% efficiency under those conditions.

C. Sample Extraction

The IOVPS is disassembled into its components. The open ends of each denuder are sealed with Teflon-lined screw caps and the denuders are then stored in a refrigerator until analysis. The filters are removed from the filter pack, and stored in plastic petri dishes or other suitable sealed containers in a freezer (−20° C.) until analysis.

At the time of extraction the denuders and filters are warmed to room temperature before extraction of the analytes. The annulus of each denuder is filled with an appropriate solvent and recapped after the addition of an appropriate internal standard for recovery.

The denuders are sonicated or subject to static, microwave or Soxhlet extraction for the time necessary to dissolve the analytes in the extraction solvent. Supercritical fluid extraction may also be used. The extract is separated from any loose sorbent particles by filtration. The extract is reduced in volume and the analytes determined by the appropriate analytical method.

The filters are extracted by contact with the appropriate solvent using sonication, microwave, Soxhlet or supercritical fluid extraction.

D. Analysis of Extracts

For analysis of polycyclic aromatic hydrocarbons, the extraction solvent was cyclohexane. The extracts were passed through Teflon filters (unlaminated, Millipore Corp.) and then silica solid-phase extraction columns (packed in glass). Before analysis the solvent was exchanged to acetonitrile by evaporating the cleaned cyclohexane extracts on silica columns (200 mg) at room temperature and eluting with acetonitrile. Final sample volume was between 250 and 1000 µl. The injection volume for high pressure liquid chromatographic (HPLC) analysis was 5 µL. Two unexposed coated denuders and pre-extracted filters were analyzed as blanks for every field test.

The extracts are passed through Teflon filters and the silica solid-phase extraction columns packed in glass. Before analysis, the solvent is exchanged to acetonitrile by evaporating the cleaned cyclohexane extracts on silica columns (200 mg) at room temperature and eluting with acetonitrile.

Extracts of the denuders are analyzed for PAH by adapting the dual-fluorescence technique developed by Mahanama et al. for analysis of semi-volatile PAH from naphthalene to chrysene *Intern. J. Environ. Anal. Chem.*, 56:289 (1994).

A Hewlett-Packard high performance liquid chromatograph Model 1090 M was used with a Vydac 201TP5215 column. The gradient program increased the eluant strength from 38% acetonitrile, 2% THF in water, to 95% acetonitrile, 5% THF, over 24 min at 0.5 mL/min. From 25 to 33 minutes the flow increased linearly to 1 mL/min. After 4.5 min the flow rate returned to 0.5 mL/min, and the mobile phase composition returned to the initial condition during the next two minutes. A 12-minute equilibration at 0.5 mL/min followed. The column was maintained at 30.8° C.

Each fluorescence detector is independently programmed to change excitation and emission wavelengths to selectively detect the PAH of interest as they elute from the column. One detector started at excitation and emission wavelengths of 220 and 348 nm, respectively, to detect naphthalene and its 1- and 2-methyl derivatives, acenaphthene and acenaphthylene. At 11.5 minutes it is switched to 263 and 371 nm to detect chrysene. The second detector started at 246 and 296 nm to detect biphenyl and fluorene; at 11.95 minutes it switched to 245 and 359 nm to detect phenanthrene; at 16 minutes it switched to 245 and 391 nm to detect pyrene; and at 21.7 minutes it changed to 288 and 405 nm to detect benz(a)anthracene. These fluorescence programs were developed by studying the excitation and emission spectra of standard compounds to select conditions of both high sensitivity and selectivity. However, during the field testing with environmental tobacco smoke several modifications were made, as described above, to overcome real-world interferences from other PAH and their alkyl derivatives. The detection and quantitation limits for both the gas and particle phases, derived from analysis of blanks, are shown in Table 4. Recovery of both internal standards from denuder extracts averaged 70%. PAH concentration data were corrected for the observed recovery. Extracts of filters were analyzed for PAH using the dual-fluorescence detector technique of Mahanama, ibid (1994).

TABLE 4

Detection and Quantitation Limits for Semi-Volatile PAH

| PAH | LLD(a) ng | LLQ(b) ng | LD(a, c) ng/m$^3$ | LLQ(b, c) ng/m$^3$ |
|---|---|---|---|---|
| Gas phase | | | | |
| Naphthalene | 13 | 44 | 43 | 130 |
| 1-Methylnaphthalene | 4.8 | 16 | 16 | 48 |
| 2-Methylnaphthalene | 19 | 62 | 63 | 190 |
| Biphenyl | 31 | 105 | 105 | 315 |
| Acenaphthene & acenaphthylene | 1.6 | 5.5 | 5.3 | 16 |
| Fluorene | 2.9 | 9.7 | 9.7 | 29 |
| Phenanthrene | 6.4 | 21 | 21 | 64 |
| Anthracene | 0.06 | 0.19 | 0.2 | 0.6 |
| Fluoranthene | 0.5 | 1.7 | 1.7 | 5.0 |
| Pyrene | 0.5 | 1.7 | 1.7 | 5.0 |
| Benz (a) anthracene | 0.03 | 0.1 | 0.1 | 0.3 |
| Chrysene | 0.22 | 0.7 | 0.7 | 2.2 |
| Particulate phase | | | | |
| Naphthalene | 5.2 | 18 | 17 | 52 |
| 1-Methylnaphthalene | 3.5 | 12 | 12 | 35 |
| 2-Methylnaphthalene | 3.1 | 10 | 10 | 31 |
| Biphenyl | 0.74 | 2.2 | 2.5 | 7.4 |
| Acenaphthene & acenaphthylene | 0.42 | 1.4 | 1.4 | 4.2 |
| Fluorene | 0.37 | 1.2 | 1.2 | 3.7 |
| Phenanthrene | 1.6 | 5.2 | 5.2 | 16 |
| Anthracene | 0.04 | 0.1 | 0.1 | 0.4 |
| Fluoranthene | 1.3 | 4.5 | 4.5 | 13 |
| Pyrene | 0.42 | 1.4 | 1.4 | 4.2 |
| Benz (a) anthracene | 0.015 | 0.05 | 0.1 | 0.2 |
| Chrysene | 0.32 | 1.1 | 1.1 | 3.2 |

(a) The lower limit of detection (LLD) is estimated as 3 × the standard deviation observed for the blanks.
(b) The lower limit of quantitation (LLQ) is estimated as 10 × the standard deviation observed for the blanks
(c) LLD and LLQ for 0.3 m$^3$ air sample (1 hour sampling at 5 L/min).

E. Comparison to Filter-Sorbent Bed Sampling

Conventional samplers were constructed with a 47-mm diameter filter followed by a sorbent trap that contained between 0.15 and 2.5 cleaned unground XAD-4 resin beads (20–60 mesh). In several experiments the filter-sorbent bed sampler was co-located indoors with the IOVPS and operated for the same time and at the same flow rate. Because the two sampler types could yield different phase distributions of all but the most volatile PAH (due to the possibility of both positive and negative artifacts expected from the conventional sampler), only species more volatile than phenanthrene, i.e., the naphthalenes, acenaphthene, acenaphthylene and fluorene would be expected to be trapped with the same efficiency by both sampler types. Gas phase concentrations of these PAH were determined from the co-located samplers.

Data from sampling indoor laboratory room air at 20 L/min for 3 hours are presented in Table 5.

TABLE 5

Comparison of IOVPS to Sorbent Bed for Collection of Gas Phase PAH (a)

| PAH | Denuder ng/m$^3$ | Sorbent ng/m$^3$ | Den/Sorb ratio | LLD for Den(b) ng/m$^3$ |
|---|---|---|---|---|
| Napthalene | 545 | 798 | 0.68 | 2.9 |
| 1-Methylnaphthalene | 161 | 202 | 0.80 | 0.7 |
| 2-Methylnaphthalene | 220 | 315 | 0.70 | 1.5 |

TABLE 5-continued

Comparison of IOVPS to Sorbent Bed for Collection of Gas Phase PAH (a)

| PAH | Denuder ng/m³ | Sorbent ng/m³ | Den/Sorb ratio | LLD for Den(b) ng/m³ |
|---|---|---|---|---|
| Biphenyl | 61.6 | 102 | 0.60 | 3.2 |
| Acenaphthene and Acenaphthylene | 18.3 | 25.4 | 0.72 | 0.1 |
| Fluorene | 17.0 | 19.9 | 0.85 | 0.5 |
| Phenanthrene | 38.4 | 41.5 | 0.93 | 1.9 |
| Anthracene | 0.61 | 0.64 | 0.95 | 0.11 |
| Fluoranthene | 6.06 | 7.25 | 0.84 | 0.74 |
| Pyrene | 2.33 | 2.98 | 0.78 | 0.68 |
| Chrysene | 2.01 | 3.34 | 0.60 | 0.92 |
| Average (Naph - Fluorene) | | | | 0.73 |
| Average (Phen - Chry) | | | | 0.82 |

(a) Indoor laboratory room air sampled at 20 L/min for 3 hours; air volume = 3.7 m³.
(b) The LLD was calculated from the observed variability of two unused denuders.

The PAH concentrations observed in this experiment were the highest indoor concentrations encountered in this study, and the capacity of the IOVPS in the configuration shown in FIG. 1 was exceeded for the most volatile species. The IOVPS-derived PAH concentrations averaged 73±9% of the sorbent-derived concentrations for PAH more volatile than phenanthrene, namely the naphthalenes, acenaphthylene, biphenyl and fluorene. The observed differences in concentrations of the naphthalenes are consistent with a deficit of about 25% in collection of the naphthalenes by the IOVPS at 20 L/min that can be deduced from the data of FIG. 8. Since the IOVPS was operated at a flow rate above its optimal setting, incomplete trapping and/or losses of the most volatile species were not unexpected and are consistent with the results presented in Table 3 and FIG. 8. Denuder-derived concentrations for phenanthrene and the less volatile PAH from the IOVPS averaged 82±14% of the sorbent-derived values for the same experiment. However, phenanthrene and less volatile species may show "blow-off" artifacts that increase apparent sorbent bed concentration. Since the data presented in FIG. 8 indicate that phenanthrene was collected in the three denuders with greater than 90% efficiency even under the sampling conditions of this experiment, and since the denuders have higher efficiency for the less volatile PAH, the lower gas-phase concentrations measured with the denuder for fluoranthene, pyrene, and chrysene are consistent with "blow-off" artifact from the particle-loaded filter in the filter-sorbent bed sampler.

The available data indicate the IOVPS traps and recovers semi-volatile PAH quantitatively when its capacity is not exceeded. This conclusion is consistent with the results obtained by other workers who are evaluating the IOVPS in chamber studies of PAH reactions in the presence of combustion effluents. Fan et al, presentation at the International Symposium on Toxic and Related Air Pollutants, Durham, N.C. (1993) subsequently published in *Atmospheric Environment*, 29:1171 (1995), found that the concentrations of the naphthalenes, sampled at 20 L/min for 20 minutes, obtained with the IOVPS agreed with those seen in a filter-sorbent bed sampler that used polyurethane foam as the trapping agent for gas-phase PAH.

V. Efficiency and Capacity of the Samplers

A. Performance of the Integrated Organic Vapor-Particle Sampler of the Invention The efficiency of a sorbent-based sampler according to the invention depends on the concentrations of the sorbed species in the airstream. At low concentrations the volumetric capacity depends on the total volume of air sampled and is independent of the gas-phase concentrations of the sorbed species. The holding power or efficiency of the trap is limited by the amount of air necessary to elute or displace adsorbed material from the surface, as occurs in gas-solid chromatography. At higher inlet gas-phase concentrations the adsorption sites could be filled before the volumetric capacity is exceeded because the weight capacity of the sorbent has been reached. The gas-phase PAH concentration data obtained from sampling indoor air under various conditions have been used to estimate these limits for the IOVPS. The aim of these studies was to find useful operating range rather than investigating the sorption mechanism in detail.

For efficiency and capacity determinations, it was assumed that the volumetric capacity Vg for a particular PAH had been exceeded for total air volumes for which the first denuder collected less than 90% of that PAH. The concentrations of all PAH were determined separately in each denuder section. The percentages of naphthalene and its methyl derivatives, fluorene and phenanthrene found on the first of the three serial denuders are shown in Table 6.

Table 6 presents the percentage recoveries on the first of three denuders in series for naphthalene with its methyl derivatives, fluorene and phenanthrene in series versus flow rate and sampling duration.

TABLE 6

Percent Recovery of PAH on the First of Three Denuders

| Sampling time | Flow rate, L/min | | |
|---|---|---|---|
| hours | 5 | 10 | 20 |
| Naphthalene | | | |
| 3 | 99 | 93 | 44 |
| 6 | 93 | 88 | 42 |
| Fluorene | | | |
| 3 | 100 | 96 | 75 |
| 6 | 93 | 78 | 71 |
| Phenanthrene | | | |
| 3 | 100 | 97 | 81 |
| 6 | 89 | 91 | 77 |

(a) Based on sampling indoor laboratory room air. Total gas - phase PAH concentration was the sum of concentrations on three denuders in series.

The total PAH concentration was assumed to be the sum of the amounts found on each denuder. This assumption may have underestimated naphthalene concentrations for sampling at 20 L/min based on the data shown in FIG. 8, described below. Based on this data, each single-channel denuder section of 22 mm length, as described above, may be advantageously used upstream of the filter to sample up to 1.8 m³ indoor air, equivalent to 10 L/min for 3 hours or 5 L/min for 6 hours. Therefore, quantitative collection of naphthalene and other semi-volatile PAH from 3.6 m³ can be done with two denuders in series at 10 L/min for 6 hours or at 20 L/min for 3 hours. Alternatively, a single 5-channel denuder with 22 cm length could be used to sample up to a total volume of 5.4 m³, but some particle loss may occur. A single-channel denuder of increased length could also be used to increase trapping capacity. Results seen in FIG. 8 suggest that four denuder sections would trap at least 95% of fluorene, phenanthrene, and less volatile species at 20 L/min during 6 hours of sampling.

FIG. 8 shows semi-logarithmic plots of several gas-phase PAH as a function of denuder position, for various flow rates and two sampling times. Specifically, FIG. 8 shows semi-logarithmic plots of PAH concentration data for naphthalene, 1-methylnaphthalene, fluorene and phenanthrene versus denuder position in the sampling train.

Positions 1, 2 and 3 correspond to 22, 24 and 26 in FIG. 1. FIG. 8 designators represent flow rates as follows: open squares: 20 L/min, 3 hr; closed squares: 20 L/min, 6 hr; open diamonds: 10 L/min, 3 hr; closed diamonds: 10 L/min, 6 hr; open triangles: 5 L/min, 3 hr; and closed triangles 5 L/min, 6 hr.

The solid line shows trapping of 90% of each PAH on the first (upstream) denuder wherein (a) is naphthalene; (b) is 1-methylnaphthalene; (c) fluorene and (d) is phenanthrene.

Position 1 refers to the denuder closest to the cyclone. Data for each experiment were normalized so that the amount of each PAH on the first denuder was 100 arbitrary units.

The data for 2-methyl naphthalene were between those for naphthalene and 1-methylnaphthalene. The naphthalenes were not trapped as effectively at 20 L/min as at 10 and 5 L/min. At 10 L/min logarithms of the concentrations of the naphthalenes on each section were linear with denuder position indicating exponential decay of gas-stream concentrations. No naphthalenes were detected on the third denuder section when the flow rate was 5 L/min. Fluorene and phenanthrene were collected on the third denuder only at 20 L/min, at which flow rate their concentration dependence also appeared to be exponential. Fluorene and phenanthrene were not detected on the second denuder for sampling at 10 L/min for 3 hours or for either sampling duration at 5 L/min. Each section of the figure has a line drawn to indicate 90% recovery of each species on the first denuder for assumed exponential decrease of gas stream concentration versus denuder position.

As seen in FIG. 8, the method has a good reproducibility and the four denuder IOVPS was able to trap more than 95% of PAH.

Based on the results presented above it may be concluded that the optimal flow rates for routine operation of the IOVPS, when it is assembled with single channel denuders of the diameter use here, are 5–10 L/min. Optimal sampling time will depend on the concentration range expected, the denuder coating mass and total length of the pre-filter section. In these studies 3 hours were sufficient to trap PAH in indoor laboratory room air at 5 and 10 L/min. Two pre-filter denuders should be used when capacity limits for a single denuder may be exceeded. Sampling at 20 L/min with three or four denuders in series can also be used when naphthalene is not of interest. At this higher flow rate, a larger sample of particles is collected, and lower limits of detection result for both particulate and gas phase PAH.

Volumetric capacity ($V_g$) is about 2 m$^3$ per denuder section for these compounds. The data indicate that $V_g$ is somewhat higher for sampling at 10 L/min for 3 hours, compared to sampling, at 5 L/min for 6 hours. Apparently greater displacement or elution of PAH occurred at the combination of lower flow rate (longer residence time) and longer total sampling time. This result suggests that volumetric capacity depends on face velocity.

Lower limits to the weight capacity of the ground XAD-4 for several PAH were estimated from the amounts of these compounds collected on the first and sometimes second of three denuders in series under conditions where breakthrough was observed. The XAD-4 coating mass was measured for each denuder section. For the purposes of the estimate, breakthrough was assumed to have occurred when the amount trapped on the next downstream denuder was more than 10% of the total found on all three denuder sections. Based on this operational definition, breakthrough of naphthalene onto the second denuder was seen at 20 L/min for 3 hours of sampling and at 10 L/min for 6 hours of sampling.

Breakthrough of naphthalene from the second denuder to the third denuder section occurred when the IOVPS operated at 20 L/min for 6 and 22 hours. Under those conditions naphthalene migrated axially along the denuder sections during the extended sampling period, so the volumetric capacity was exceeded. Breakthrough was not observed at 20 L/min for four-ring PAH. For the other PAH, breakthrough occurred only when sampling at 20 L/min for 3 hours or longer. The observed breakthrough shows that migration along the denuder sections dominated the collection efficiency for the most volatile species, even though their higher diffusivities compared to the heavier PAH would predict more efficient collection in a diffusion denuder.

The weight capacity of ground XAD-4 for naphthalene, fluorene and phenanthrene, sampled together with other PAH, in indoor air was found to be (±standard deviation; n=the number of observations) 57±16 (n=8), >4.3+1.3 (n=3), and >7.7±3.4 (n=5) ng/mg XAD-4, respectively. The high standard deviations reflect the fact that some of the denuders were too long to fit within the weighing compartment of the analytical balance and had to be weighed on a pan balance to the nearest 10 mg. Therefore, the coating mass was known only to only one significant figure in those cases. The value found here for naphthalene is about 3 times higher than estimated from breakthrough experiments for an XAD-4 resin sorbent sampler. A typical denuder section can trap about 800 ng naphthalene, 50 ng fluorene and 100 ng phenanthrene.

B. Assessment of TOVPS Performance

The performance of the IOVPS is assessed by using the models for annular denuder efficiency developed by Possanzini et al., and described in *Atmospheric Environment*, 16:845–853, (1983) and Coutant, et al., *Atmos. Environ.*, 23:2205 (1989). The Possanzini model applies to a surface coating that irreversibly reacts with the gas-phase component of interest. Coutant considers denuder performance when the reaction or adsorption probability is less than one for each collision of the gas-phase component with the denuder coating. Both models predict that, for sufficient denuder length, the ratio of outlet to inlet concentration for a trapped component of the airstream follows an exponential dependence on the ratio of denuder length to the total air flow.

For a single denuder section of length L the outlet concentration ($C_{out}$) of the gas phase component has been reduced from the inlet concentration ($C_{in}$) of the gas phase component by the amount of the gas phase component trapped on the denuder surface, per unit volume of air. The efficiency is $1-(C_{out}/C_{in})$.

For an IOVPS with several denuders the efficiency of the first section $E_1$ can be approximated by assuming that $C_{in}$ is the sum of the amounts of gas phase component per m³ found on each section $C_1, C_2, \ldots C_n$, where n is the number of denuder sections. The outlet concentration after the first section is the difference between $C_{in}$ and $C_1$. Therefore, the efficiency of one section is $$E_1 = 1 - \frac{C_{out}}{C_{in}} = \frac{C_1}{C_{in}} \quad (1)$$

and the efficiency of two sections (used together) is $$E_2 = \frac{C_1 + C_2}{C_{in}} \quad (2)$$

Practical use of these models for efficiency measurements is illustrated in FIG. 9.

FIG. 9 shows semi-logarithmic plots of outlet concentration $C_{out}$ to inlet concentration $C_{in}$ several gas-phase PAH concentrations as a function of denuder length to the volume of sampled air, for various flow rates and two sampling times.

The solid line shows trapping of 90% of each PAH on the inlet concentration for each denuder represent: (a) naphthalene; (b) 1-methylnaphthalene; (c) fluorene; and (d) phenanthrene.

FIG. 9 designators are as follows: downward triangles, 5 L/min, 3 hr; upward triangles, 5 L/min, 6 hr; open squares: 10 L/min, 3 hr; open diamonds: 10 L/min, 6 hr; open horizontal hexagons: 20 L/min, 3 hr; and open vertical hexagons: 20 L/min, 6 hr. For naphthalene and methylnaphthalene sampled at 20 L/min, $C_{in}$ was taken from the filter-sorbent bed sampler data.

FIG. 9 shows semi-logarithmic plots of $C_{out}/C_{in}$ for collection of several PAH versus the ratio of denuder length to the volume or air that passed through the IOVPS. The solid and open symbols correspond to the length of one and two sections, respectively. For one section, $C_{out}/C_{in}=(C_{in}-C_1)/C_{in}$. The solid symbols show $(C_{in}-C_1)/C_{in}$ versus L1/V, where L1 is the length of the first section and V is the total volume of air sampled. The open symbols give the data for two sections: $C_{in}-[(C_1+C_2)/C_{in}]$, versus (L1+L2)/V. Data are shown for naphthalene, 1-methylnaphthalene, fluorene and phenanthrene samples in indoor air at flow rates of 5, 10, and 20 L/min for 3 and 6 hours. $C_{in}$ for 20 L/min includes the difference between amounts found on the denuder and parallel sorbent bed samples, i.e., the amounts not trapped by the three denuder sections of the IOVPS. The line drawn in each section of the figure corresponds to the predicted exponential decay for a theoretical efficiency of 90% for each section when the IOVPS operates at 10 L/min for 3 hours sampling (or 5 L/min for 6 hours). The ordinate value of 0.1 corresponds to 90% efficiency.

Besides confirming the volumetric gas capacity of 2 m³ per denuder section for 90% efficiency, the data suggest that $C_{out}/C_{in}$ is an exponentially decaying function of the ratio of denuder length to air volume, consistent with the models of Possanzini and Coutant. Efficiency improved as the molecular weight increased from naphthalene to fluorene while the vapor pressure decreased. For naphthalene, besides diffusion and adsorption, axial migration also influenced the collection efficiency for sampling at 20 L/min.

C. Design Criteria for IOVPS

A spreadsheet template has been created for calculation of the theoretical efficiency of an annular denuder with dimensions of GAP sample using the Possanzini equation, where:

CO=initial gas-phase concentration;
C=gas-phase concentration after passage through the denuder with annulus $d_2-d_1$;
$d_1$=inner diameter of the annulus in cm;
$d_2$=outer diameter of the annulus in cm²/sec;
D=the diffusion constant of the adsorbed species, in cm²/sec;
L=length of the coated section;
F=flow rate in cm³/sec;

The efficiency according to this calculation is defined as:

$$E=100(1-C/C_O) \text{ where}$$

C/Co=0.82 exp (−22.53 delta$_a$); and
delta$_a$=pi D L $(d_1+d_2)/[4F(d_1-d_2)]$.

An example spreadsheet for the hybrid IOVPS-GAP sampler appears in Table 7, given below. Table 7 represents an efficiency calculation for naphthalene, which has D=0.081 cm²/sec at room temperature.

TABLE 7

Naphthalene at Room Temperature

| Annulus Flow | Flow Diam. (cm) | Inside $N_{Ra}$ Area (cm²) | Inside Std Diam. (cm) | Outside C/C₀ Area (cm²) | Width (cm) | Outside Sect. Area (cm²) | Volume (cm³) | Annulus | (L/min) | Cross % Total | Annulus (cm³/s) | | Flow Deviat. (%) |
|---|---|---|---|---|---|---|---|---|---|---|---|---|---|
| (a) | 0.20 | 34.56 | 0.60 | 103.67 | 0.20 | 0.25 | 15.08 | 0.35 | 5.86 | 2.10 | 61.33 | 1.19 | 1.669E−1 |
| (b) | 0.80 | 138.23 | 1.26 | 217.71 | 0.23 | 0.74 | 44.65 | 1.04 | 17.34 | 6.23 | 70.52 | 0.90 | 1.184E−09 |
| (c) | 1.50 | 259.18 | 1.90 | 328.30 | 0.20 | 1.07 | 64.09 | 1.49 | 24.89 | 8.94 | 61.33 | 1.19 | 1.669E−12 |
| (d) | 2.20 | 380.13 | 2.64 | 456.16 | 0.22 | 1.67 | 100.36 | 2.34 | 38.98 | 14.00 | 67.46 | 0.99 | 1.784E−10 |
| (e) | 3.00 | 518.36 | 3.40 | 587.48 | 0.20 | 2.01 | 120.64 | 2.81 | 46.85 | 16.83 | 61.33 | 1.19 | 1.669E−12 |
| (f) | 3.80 | 656.59 | 4.40 | 760.26 | 0.30 | 3.86 | 231.85 | 5.40 | 90.05 | 32.35 | 91.99 | 0.53 | 5.216E−06 |
| (g) 21 | 4.80 | 829.38 | 5.10 | 881.22 | 0.15 | 2.33 | 139.96 | 3.26 | 54.36 | 19.53 | 45.99 | 2.12 | 1.347E− |
| | | 2816.44 | | 3334.80 | | | 11.94 | 716.62 | 16.70 | 278.33 | | 100.00 | |

C = initial concentration
C₀ = concentration after denuder
D = diffusion coefficient in cm²/sec
L = coating length in cm
F = flow rate in the tube/annulus (cm³/sec)

Spreadsheets of this type have been used for prediction of the collection efficiency of denuders of various dimensions. The theoretical efficiencies assume perfect retention of the species of interest such as occurs for the chemical reaction of HONO at a denuder surface coated with sodium carbonate. The actual efficiency of a denuder that traps by adsorption will be reduced by a factor that must be determined experimentally.

VI. Laboratory and Field Testing

Assembly of the equipment used for field testing is described in Section I. Coating was prepared and impurities were removed according to Section II. Electron microscopy was tested using procedure of Section II. E. Extraction of analytes and analysis was performed according to Section III.

Extracts of the denuders were analyzed for PAH by adapting the dual-fluorescence technique developed by Mahanama et al. for analysis of semi-volatile PAH from naphthalene to chrysene *Intern. J. Environ. Anal. Chem.*, 63: (1994). A high performance liquid chromatograph Hewlett Packard Model 1090 M was used with a Vydac 201TP5215 column. The gradient program increased the eluant strength from 38% acetonitrile, 2% THF in water, to 95% acetonitrile, 5% THF, over 24 min at 0.5 mL/min. From 25 to 33 minutes the flow increased linearly to 1 mL/min. After 4.5 min the flow rate returned to 0.5 mL/min, and the mobile phase composition returned to the initial condition during the next two minutes. A 12-minute equilibration at 0.5 mL/min followed. The column was maintained at 30.8° C.

A. PAH Concentrations in Indoor Air and Simulated ETS

Table 8 summarizes the gas phase concentration data obtained with the IOVPS for indoor air with no combustion sources and simulated ETS. The ranges and average concentrations are listed. PAH concentrations were typically at least three times higher in ETS than in the relatively clean room air of the laboratory. The concentration ranges are similar to those reported by other workers for indoor air with ETS.

TABLE 8

Concentration Ranges for Gas Phase PAH in ng/m³

| PAH | Indoor air | | | Environ. Tobacco Smoke | | |
|---|---|---|---|---|---|---|
| | Min. | Max. | Avg. | Min. | Max. | Avg. |
| Naphthalene | 162 | 545 | 338 | 784 | 1690 | 1099 |
| 1-Methylnaphthalene | 43 | 161 | 89 | 334 | 748 | 485 |
| 2-Methylnaphthalene | 67 | 220 | 142 | 526 | 931 | 719 |
| Biphenyl | 4.1 | 62 | 25 | 45 | 423 | 189 |
| Acenaphthene & acenaphthylene | 3.3 | 18 | 8.3 | 2.7 | 134 | 70 |
| Fluorene | 4.1 | 17 | 8.2 | 57 | 267 | 129 |
| Phenanthrene | 18 | 38 | 23 | 43 | 151 | 99 |
| Anthracene | 0.1 | 0.6 | 0.4 | 3.9 | 22 | 13 |
| Fluoranthene | 3.5 | 9.8 | 6.5 | 3.7 | 13 | 10 |
| Pyrene | 2.2 | 4.6 | 3.0 | 14 | 64 | 44 |
| Benz (a) anthracene | 0.1 | 0.1 | 0.4 | 0.2 | 1.1 | 0.4 |
| Chrysene | 0.8 | 2.0 | 1.4 | 0.9 | 10 | 5.8 |

B. Phase Distributions and "Blow-off" of PAH in Indoor Laboratory Room Air

Table 9 below presents phase distribution data for phenanthrene, pyrene and chrysene in indoor laboratory room air samples collected at 20 L/min for 3 hours (filter face velocity=33 cm/sec) during which the IOVPS and a filter-sorbent bed sampler operated for 3 hours.

TABLE 9

Phase Distributions of PAH in Indoor Laboratory Room Air

| PAH | IOVPS | Filt-Sorb |
|---|---|---|
| Phenanthrene | 0.097 | 0.033 |
| Pyrene | 0.157 | 0.053 |
| Chrysene | 0.247 | 0.052 |

(a) Indoor laboratory room air sampled at 20 L/min for 3 hours

The particulate fractions were much lower for this environment than for ETS, but the sampling conditions, face velocities and sampling times, as well as the chemical composition, were very different. The particulate fractions obtained with the filter-sorbent bed sampler were smaller for all three PAH than obtained using the IOVPS. The discrepancy decreased as the PAH volatility decreased. Two other parallel sampling experiments also yielded pre-sorbent-bed filter samples that had lower PAH concentrations than the filter samples obtained with the IOVPS. The data are consistent with PAH volatilization from the particles ("blow-off") during sampling with the filter-sorbent bed. Post-filter denuders were not used with the IOVPS in these experiments, so blow-off from the IOVPS-collected particles could not be assessed. However, in a separate experiment using the configuration shown in FIG. 2 at face velocity of 17 cm/sec (10 L/min, 6 hours) detectable amounts of phenanthrene, pyrene, benz(a)anthracene and chrysene were found an a post-filter denuder. Since these compounds were not detected on the second denuder, they must have desorbed from the particles during sampling.

C. Simulated Field Test for Phase Distributions for PAH in Environmental Tobacco Smoke Simulated environmental tobacco smoke was sampled at 16 and 20° C. in a sealed (0.03 air exchange per hour, measured by $SF_6$ injection) 36 m³ environmental chamber. A smoking machine (Arthur D. Little, Inc.,) was used in the center of the room, about 4 feet above the floor. Three reference cigarettes, Kentucky reference type 1R4F were machine-smoked sequentially at one 35 mL puff per minute. The mainstream smoke was ventilated outside the chamber, while the side stream smoke was emitted into the chamber. Two IOVPSs were placed about 2 feet apart, with their inlets about two feet above the floor. The samplers operated for one hour at 5 L/min starting about 20 minutes after the last cigarette was extinguished. A filter-sorbent bed sampler was located about 2 meters from the IOVPS and operated at 5 L/min during the same period.

In a separate experiment in the 36 m³ chamber just one IOVPS operated under the same conditions. A different chamber (20m³) was also used to sample ETS with the IOVPS for method development. In that chamber four commercial filter cigarettes were machine-smoked using the same smoking cycle (one every 25 minutes) over a 2 hour period the IOVPS operated at 5 L/min for one hour during that time.

Table 10 presents phase distribution data for simulated environmental tobacco smoke sampled at 16° C.

TABLE 10

Phase Distributions of PAH in Environmental Tobacco Smoke

| PAH | gas ng/m$^3$ | particles ng/m$^3$ | fraction in particles |
|---|---|---|---|
| Naphthalene | 822 | <17 | <0.02 |
| 1-Methylnaphthalene | 334 | <12 | <0.04 |
| 2-Methylnaphthalene | 526 | <10 | <0.02 |
| Acenaphthene & acenaphthylene | 72.2 | <1.4 | <0.02 |
| Fluorene | 56.5 | <1.7 | <0.02 |
| Phenanthrene | 43.1 | <5.2 | <0.11 |
| Anthracene | 3.85 | <0.1 | <0.03 |
| Fluoranthene | 3.73 | 2.3 | 0.38 |
| Pyrene | 13.8 | 3 | 0.18 |
| Benz (a) anthracene | 0.15 | 10.4 | 0.99 |
| Chrysene | 0.86 | 30.1 | 0.97 |

(a) Sampled at 5 L/min for 1 hour

Both gas and particle phase data are average values for the co-located samplers when the IOVPS operated in the 36 m$^3$ chamber for one hour at 5 L/min with face velocity =8 cm/sec. None of the more volatile PAH from naphthalene to anthracene were detected on the ETS particles, but fluoranthene and pyrene were found in both phases. Very little benz(a)anthracene and chrysene were found in the gas phase for ETS. Generally, the particulate fraction increased as molecular weight increased and vapor pressure decreased. No detectable amounts of PAH were found on the second filters or the post-filter denuders. No "blow-off" of particulate PAH onto the backup filter substrate or downstream denuder was observed for this experiment. In a separate experiment using the same IOVPS configuration but with the chamber at 20° C., fluoranthene, pyrene and chrysene were detected on the post-filter denuder, indicating that some blow-off occurred. The amounts found on the post-filter denuder averaged 16% of the total particulate PAH concentrations.

F. Limits of Detection

Because of the development of a new cleanup technique and the sensitivity of a newly-developed dual fluorescence detector high performance liquid chromatography method, good precision has been obtained with the sampler, for determination of the phase distribution of PAH in indoor air and ETS, in as little as one hour of sampling. Detection limits for phenanthrene, anthracene, pyrene and chrysene were 10, 0.1, 0.8 and 0.4 ng/m$^3$ respectively, for gas phase concentrations. Particulate phase detection limits for the same compounds were 2.6, 0.5, 0.7 and 0.5 ng/m$^3$, respectively for single channel IOVPS at flow rates of 10 L/min.

G. Reproducibility of PAH Concentration Measurements

Reproducibility of PAH concentration measurement was determined and results are seen in Table 11.

Table 11 presents PAH concentrations obtained from two co-located IOVPS that simultaneously sampled simulated environmental tobacco smoke. For denuder extracts of the upstream denuder the coefficient of variation ranged from 5% for 1-methylnaphthalene to 31% for pyrene and averaged 14%. The high value for pyrene could be due to its co-elution with one of the methyl derivatives of phenanthrene. The fluorescence excitation and emission wavelengths for pyrene were chosen from the edges of its response envelope so that the methylphenanthrene interference was minimized. The poor quantum yield for pyrene under that condition probably contributed to its high variability. The higher-than-average coefficient of variation for biphenyl may be due to its co-elution with 2-methylnaphthalene which was always found at higher concentrations that biphenyl. Most of the semi-volatile PAH were not detected in the particle phase. However, the four that were detected had average coefficient of variation of 16%.

TABLE 11

Reproducibility of PAH Concentration Measurements in Simulated Environmental Tobacco Smoke

| | Gas phase | | | Particle phase | | |
|---|---|---|---|---|---|---|
| PAH | Avg. ng/m$^3$ | Std Dev ng/m$^3$ | Coeff of Var. | Avg. ng/m$^3$ | Std Dev ng/m$^3$ | Coeff of Var. |
| Naphthalene | 822 | 82 | 9.9 | bd | — | — |
| 1-Methyl-naphthalene | 334 | 18 | 5.4 | bd | — | — |
| 2-Methyl-naphthalene | 526 | 40 | 7.6 | bd | — | — |
| Biphenyl | 45 | 10 | 21.6 | bd | — | — |
| Acenaphthene and acenaphthylene | 72 | 12 | 16.5 | bd | — | — |
| Fluorene | 56.5 | 3.6 | 6.4 | bd | — | — |
| Phenanthrene | 43.1 | 6.7 | 15.5 | bd | — | — |
| Anthracene | 3.85 | 0.53 | 13.8 | bd | — | — |
| Fluoranthene | 3.73 | 0.53 | 14.2 | 2.3 | 0.07 | 3.1 |
| Pyrene | 13.8 | 4.3 | 30.9 | 3.0 | 0.3 | 11.1 |
| Benz (a) anthracene | 0.15 | 0.028 | 18.8 | 10.4 | 3.7 | 35.1 |
| Chrysene | 0.86 | 0.067 | 7.8 | 30.1 | 3.5 | 11.7 |
| Average: | | | 14.0 | | | 15.2 |
| Std Dev: | | | 7.4 | | | 13.8 | bd = below the lower limit of detection

E. Comparison of the IOVPS to a Filter-Sorbent Bed Sampler

Comparison of the IOVPS to a filter-sorbent bed sampler for collection of gas-phase PAH in indoor air at two flow rates is shown in Table 12.

TABLE 12

Comparison of the IOVPS to a Filter-Sorbent Bed Sampler[a]

| PAH | Uncertainty % | Denuder/Sorbent ratio 10 L/min | Denuder/Sorbent ratio 20 L/min |
|---|---|---|---|
| Naphthalene | 11.0 | 0.83 ± 0.09 | 0.68 ± 0.07 |
| 1-Methylnaphthalene | 11.7 | 1.11 ± 0.13 | 0.80 ± 0.09 |
| 2-Methylnaphthalene | 11.7 | 1.03 ± 0.12 | 0.70 ± 0.08 |
| Biphenyl | 22.7 | 1.03 ± 0.23 | 0.60 ± 0.13 |
| Acenaphthene and acenaphthylene | 14.0 | 0.87 ± 0.12 | 0.72 ± 0.10 |
| Fluorene | 30.4 | 0.95 ± 0.29 | 0.85 ± 0.26 |
| Phenanthrene | 14.5 | 1.18 ± 0.17 | 0.94 ± 0.14 |
| Anthracene | 12.7 | 0.94 ± 0.12 | 0.95 ± 0.12 |
| Fluoranthene | 12.7 | 1.00 ± 0.13 | 0.84 ± 0.11 |
| Pyrene | 29.6 | 1.05 ± 0.31 | 0.84 ± 0.25 |
| Chrysene | 20.4 | bd[b] | 0.65 ± 0.13 |
| Average (All PAH) | | 1.00 ± 0.10[c] | 0.78 ± 0.12[c] |

[a]Three-hour sampling periods on two different days
[b]Below the detection limit
[c]Standard deviation derived from the average of denuder/sorbent ratios Comparison data from sampling indoor laboratory room air on two different days are presented in Table 12 for two flow rates, 10 and 20 L/min. Three-hour sampling periods were used for each experiment. The data indicate that the IOVPS traps and recovers semi-volatile PAH quantitatively when its capacity is not exceeded. At 10 L/min the denuders and sorbent trapped the same amounts of semi-volatile PAE. The ratio of detectable PAH measured with the denuders to PAH collected by the sorbent bed was 1.00±0.10. Therefore, the IOVPS-derived gas-phase PAH concentrations agreed with the conventional sampler results at this flow rate and sampling time. The data show no apparent sampling artifacts.

Indoor air sampling with the IOVPS for three hours at 20 L/min yielded gas-phase PAH concentrations (summed from three serial denuder sections) that averaged 78±13% of those derived from the sorbent bed. The denuder-derived PAH concentrations averaged 73±9% of the sorbent-derived concentrations for PAH more volatile than phenanthrene (the naphthalenes, acenaphthene, acenaphthylene, biphenyl and fluorene). The capacity limits for these species had been exceeded under the conditions of this experiment, as shown in FIG. 9. Denuder-derived concentrations for phenanthrene and the less volatile PAH from the IOVPS averaged 84±13% of the sorbent-derived values for the same experiment. That average is heavily dependent on the value for chrysene, but the gas phase concentrations of chrysene for the two sample types are well above the limits of quantitation and appear to be statistically different. Since the data of FIG. 9 indicate that phenanthrene was collected in the first two of three denuder sections with >90%-efficiency under the sampling conditions of this experiment, operation of the IOVPS with three serially-connected sections is expected to lead to >99% efficiency. However, the apparent sorbent bed concentration may have been increased by "blow off" artifacts from the filter-collected particulate phenanthrene and less volatile species fluoranthene through chrysene.

EXAMPLE 1

Field Test for Nicotine in Environmental Tobacco Smoke

The IOVPS was used in the configuration shown in FIG. 2 to determine nicotine in simulated environmental tobacco smoke. This configuration was intended to collect nicotine in the denuder sections and on the filter. Any nicotine blown-off the filter was trapped by the downstream denuder section. The denuder sections had been coated with ground XAD-4 resin as described above. Denuders were coated with XAD-4 as described above. Denuders were extracted by sonication with spectroscopic-grade ethyl acetate with 0.01% triethylamine. The triethylamine prevents adsorption of nicotine to glass surfaces. Quinoline was added at the time of extraction as an internal standard to correct for any volatility losses during sample preparation. The extracts were filtered with a Millipore Teflon filter of pore size 0.5 micrometers, filter type FHUP, to separate the XAD-4 coating from the extracts. The extracts were concentrated to approximately 500 microliters.

Extracts of denuders were analyzed for nicotine using a nitrogen-phosphorous detector mounted on a Shimadzu GC-9A gas chromatograph with a DB-Wax 30 in×0.32 mm fused silica capillary column.

The gas flow rates were: helium (primary carrier),1 mL/min; helium (make-up), 15 mL/min; hydrogen, 4 mL/min; and air, 75 mL/min. The hydrogen and air flow rates were controlled through the Shimadzu GC-9A. The helium primary carrier and make-up gases were bypassed into a Scientific Glass Engineering Unijector where their flow rates were regulated. The injector was operated in splitless mode. Both the injector port and the detector base were set to 250° C.

The column temperature program started at initial conditions of 175°C. After 5 minutes, the temperature was increased linearly at a rate of 0.5° C./min for 10 minutes until the column temperature reached 180° C.

A Detector Engineering Technology (DET) nitrogen-phosphorous detector with a ceramic thermionic source was installed on the flame ionization detector base of the Shimadzu GC-9A. Prior to sample analysis, the heating current of the DET Detector Current Supply, Model 4000, was slowly increased until ignition of hydrogen-air chemistry was achieved. Typical operating currents were approximately 3 amperes.

A Shimadzu Chromatopac C-R3A Data Processor was used to integrate peak areas during each sample run. Depending on the concentration of the sample, the sensitivity range and attenuation were manually adjusted on the Chromatopac C-R3A to optimize chromatogram output. Under these conditions, both nicotine and quinoline used as internal standard eluted between 5 and 6 minutes with excellent peak separation.

Two complete sampling trains were co-located and operated simultaneously. Three reference cigarettes were smoked sequentially in a sealed environmental chamber (36 $m^3$). About 45 minutes elapsed before sampling began. Air was pulled through the IOVPS at 5 L/min for one hour. Nicotine was determined in denuder sections and filters using the described method. The results are shown in Table 13, and they indicate that the IOVPS can be used to trap nicotine from both the gas and particle phases. Parallel sampling was conducted using Hammond et al., method (*Atmospheric Env.*, 21: 457–462, (1987).

TABLE 13

| Nicotine in Environmental Tobacco Smoke | | | |
|---|---|---|---|
| IOVPS | microgram $m^{-3}$ | Hammond | microgram $m^{-3}$ |
| Denuder d1 (gas) | 15.7 | gas | 23.6 |
| Denuder d2 | <0.24 | | |
| Filter (particles) | 0.64 | particles | 0.89 |
| Denuder d3 | <0.24 | | |

The data can be used to calculate the phase distribution of nicotine in ETS. Both gas and particulate nicotine levels measured during the same experiment with a single Hammond sampler were somewhat higher than obtained with the IOVPS.

EXAMPLE 2

Nicotine: Phase Distribution in ETS

This study was conducted in a 20 $m^3$ stainless steel environmental chamber with a surface area of 45.2 $m^2$. Six mixing fans (three inches tall) were staggered at ⅓ and ⅔ of the wall height with the axis of each fan positioned at a 45° angle from the wall surface. All fans blew air in the same circular direction around the chamber. The mixing fans were connected in series to a variable voltage controller at a setting of 50 volts and operated during, both the smoking and sampling periods. The circulation vents and chamber door were sealed with duct tape during the experiment to minimize the air exchange rate. The chamber temperature averaged 24° C., and the relative humidity was approximately 22%. A fully automated smoking machine (Lawrence Berkeley Laboratory, Berkeley, Calif.) was connected to a puffer (Model ADL/II, Arthur D. Little, Cambridge, Mass.) and positioned on the floor in the center of the room. A brand of popular filtered commercial cigarettes were conditioned at 60% relative humidity for more than 72 hours over an aqueous saturated NaBr solution. The ignition of the first cigarette was designated as zero minutes. The cigarettes were sequentially burned for approximately 11 minutes each starting at zero, 12, and 22 minutes. The cigarettes smoldered from an average length of 7.9 cm until they were extinguished at an average butt length of 3.1 cm.

Five integrated organic vapor-particle samplers inserted and removed in sequence collected nicotine for the first 189 minutes. The ventilation duct and chamber door was sealed shut with duct tape during the experiment to minimize the air exchange rate. At 189 minutes, the chamber door was opened.

Gas and particulate phase nicotine concentrations were measured as a function of time using the IOVPS which consisted of two denuders followed by two 47 mm Teflon-coated glass fiber filters. The IOVPS was inserted into the chamber through a port on the wall, and the sampler inlet extended approximately 60 cm into the room from the wall. The denuders were coated with ground XAD-4 (Alltech Associates, Inc., Deerfield, Ill.) for the collection of gas phase nicotine, with the second denuder serving, as a backup. The first glass fiber filter collected particulate nicotine, and the second glass fiber filter was cleaned and coated with an aqueous 4% $NaHSO_4$ solution (with 5% ETOH to wet the filter) for collection of gas phase nicotine blown off (or "volatilized" or "evaporated") from the particles on the upstream filter. Sampling at 5 L/min via the house vacuum regulated through a mass flow controller occurred over five periods: 9–19 min, 20–30 min, 31–41 min, 89–109 min, and 169–189 min. Newly coated denuders and clean filters were used for each sampling period. Unexposed XAD-4-coated denuders, Teflon-coated class fiber filters, and $NaHSO_4$-treated Teflon-coated glass fiber filters were set aside for blank measurements.

The denuders were extracted by filling them with ethyl acetate (approximately 20 ml) containing 0.01% v/v TEA, adding 27 $\mu$g of quinoline, and capping the ends. The denuders were then sonicated in a warm water bath (40° C.) for 15 minutes. The extracts were filtered through 47 mm Teflon filters (Type FHUP, Pore Size 0.5 $\mu$m, Millipore Corporation, Bedford, Mass.) to remove any particles of the XAD-4 denuder coating, then a second extraction and filtration was performed. The filtrates were concentrated using a rotary evaporator (Brinkmann Rotavapor -R) with a water bath set to 42° C. Final volumes ranged from 183 to 428 $\mu$l. Extracts were transferred to vials for storage and analysis.

The 47 mm Teflon-coated glass fiber filters were extracted by cutting them into 0.5 $cm^2$ pieces and placing them into a 9 ml conical vial, adding 3 ml of ethyl acetate with 0.01% v/v TEA, and spiking them with 27 $\mu$g of quinoline. The glass fiber filters were sonicated for 15 minutes and filtered using a Teflon filter. After a second extraction and filtration, the extracts were evaporated to final volumes ranging from 244 to 427 $\mu$l and transferred to vials for storage and analysis.

The 47 mm $NaHSO_4$-treated Teflon-coated class fiber filters were extracted using the method outlined by Hammond et al in *Atmospheric Env.*, 21: 457–462. (1987). Filters were spiked with 27 $\mu$g of quinoline in ethyl acetate, and approximately one minute was allowed for the ethyl acetate to evaporate at room temperature. The intact 47 mm $NaHSO_4$-treated glass fiber filters were inserted into test tubes. To remove nicotine from the acid-coated filter, 100 $\mu$l ETOH was added to wet the filter, followed by 2 ml water. After one minute of vortexing, 2 ml of 10N NAOH was added to deprotonate nicotine in aqueous solution. The mixture was vortexed for one minute, then 500 ml ammoniated hexane was added. In a fashion similar to TEA, ammonia suppresses adsorption of nicotine onto glass. Another minute of vortexing is performed, thereby transferred nicotine to the organic hexane layer. The hexane was transferred to a vial for storage and analysis. Final volumes of hexane ranged from 190 to 310 $\mu$l.

All samples were analyzed on the day of extraction using a Shimadzu gas chromatograph obtained from Shimadzu Corporation, Kyoto, Japan. The helium primary carrier gas flow rate was set to 1 ml/min through a Scientific Glass Engineering, Unijector Control Module (SGE Inc., Austin, Tex.). Samples were injected with a 5 $\mu$l SGE syringe into the Shimadzu injector under splitless injection mode with septum purge. Injection volumes were 1.0±0.1 $\mu$l. The injector temperature was set to 250° C. Compounds were separated on a DB-WAX fused silica capillary column (30 m×0.32 mm, 0.25 $\mu$m film thickness, J&W, Folsom, Calif.). The oven temperature was pro-rammed at 165° C. for 7 minutes and then increased at 17.5° C./min to a final temperature of 200° C. for 3 minutes.

A DETector Engineering Technology (DET, Walnut Creek, Calif.) thermionic nitrogen-phosphorous detector (NPD) was mounted on top of the Shimadzu flame ionization detector base. The additional gas flow rates supplied to the detector were: helium make-up gas, 15 ml/min; hydrogen, 4 ml/min; air, 75 ml/min. The detector heating block was set to 250° C. The NPD was powered by a DET current supply (Model 4000). Operating currents used in these analyses ranged from 3.02 to 3.04 amperes. Signals were interpreted by the Shimadzu electrometer on the highest sensitivity range and plotted by the Shimadzu Chromatopac C-R3A data processor. The C-R3A processor was pro-grammed to integrate by peak area. Nicotine and quinoline eluted at approximately 5.4 min and 6.1 min respectively, with excellent peak separation. New nicotine and quinoline standards in ethyl acetate with 0.01% v/v TEA were pre-pared for the analyses, and the same standards were used for the different extractions for consistency. All extractions and analyses were completed in nine days. Nicotine and quinoline external standards were injected periodically between samples to obtain a drift correction for nicotine and quinoline response factors. Response factors decreased very slowly with time due to the decrease in sensitivity of the NPD bead with time. A linear regression analysis of the response factors was performed for each day of analysis and factored into nicotine and quinoline mass calculations for all injected samples.

All data were corrected for the percentage recovery of quinoline internal standard. Quinoline is a convenient internal standard because it is chemically similar to nicotine, but it has been reported that quinoline is present at about 1% of the nicotine concentration in ETS (Caka et al., *Environ. Sci. Technol.*, 24:1196–1206. Since quinoline was added at levels similar to the amount of nicotine found in each sampler, errors due to quinoline in ETS were negligible in most cases. However, corrections for quinoline were applied when nicotine was underestimated by more than 1%. Except where indicated, blank values were subtracted from the nicotine masses. Percent recoveries, blank masses for nicotine, limits of detection, and limits of quantitation are listed in Table 14.

TABLE 14

Results of Quinoline Phase Distribution Study

| Sampler | Recovery (%) | Blank (µg) | LOD (µg) | LOD (µg) |
|---|---|---|---|---|
| Sorbent Tubes | 65–85 | 0.12 | $4 \times 10^{-4}$ | $1.3 \times 10^{-3}$ |
| Denuders | 68–107 | 0.32 | $7 \times 10^{-2}$ | $2.5 \times 10^{-1}$ |
| 47 mm Uncoated Filters | 76–95 | b.d.* | $4 \times 10^{-4}$ | $1.5 \times 10^{-3}$ |
| 47 mm Bisulfate Filters | 44–71 | 0.08 | $5 \times 10^{-4}$ | $1.6 \times 10^{-3}$ |
| High Vol. Filter Sheets | 52–88 | b.d.* | $4 \times 10^{-4}$ | $1.3 \times 10^{-3}$ |
| Stainless Steel Sheets | 74–89 | 0.90 | $5 \times 10^{-4}$ | $1.6 \times 10^{-3}$ |

*below the limit of detection.

The gas-particle phase distribution was measured by the IOVPS system. The two denuders collected gas phase nicotine with the second denuder serving as a backup for breakthrough. The first glass fiber filter collected particle phase nicotine, and blank values were below detection so no correction was made. The second glass fiber filter was coated with 4% $NaHSO_4$ to collect volatilized nicotine from the particles on the first filter. Results are shown in Table 15.

TABLE 15

Gas Phase Distribution

| Period | Time Interval | 1st Denuder | 2nd Denuder | 1st Filter | 2nd Filter |
|---|---|---|---|---|---|
| 1 | 9–19 min | 263 | 0 | 2.7 | 0 |
| 2 | 20–30 min | 406 | 0.5 | 4.9 | 0 |
| 3 | 31–41 min | 449 | 6.3 | 5.0 | 0 |
| 4 | 89–109 min | 131 | 0 | 1.6 | 0.2 |
| 5 | 169–189 min | 74 | 0 | 4.0 | 0 |

Denuder and filter concentrations are in $\mu g/m^3$

Nicotine concentrations were taken from IOVPS gas phase measurements. Nicotine was collected in a glass sidestream smoke apparatus (225 cm³ volume), and an emission factor for the same cigarette brand was converted into an emission rate of 27.4 mg/h. The ventilation rate due to chamber leakage was determined before the experiment by monitoring $SF_6$ tracer gas decay over 13 hours. The leakage rate was 0.152 m³/h. Ventilation due to sampling was 0.232 m³/h, and the loss rate due to deposition ($v_r \times$ surface area), which is analogous to ventilation, was 0.576 m³/h. This yielded a total ventilation rate, $Q_T$, of 0.96 m³/h.

What is claimed is:

1. A method for preparation of a sorbent for sampling of semi-volatile organic gases and particulate components, said sorbent comprising macroreticular resin agglomerates of randomly packed microspheres with a continuous porous structure of particles ranging in size from 0.5 to 10 microns, said method comprising steps:
 a) preparing particles of a macroreticular resin or a combination of the macroreticular resin with an activated carbon, said particles ranging in size between 0.5 and 10 microns, by:
  i. grinding the macroreticular resin or a combination thereof with the activated carbon to the particles having a size of 10 microns or lower;
  ii. suspending said ground macroreticular polymeric resin or the combination thereof in an organic solvent,
  wherein said resin is selected from the group consisting of a styrene divinylbenzene polymer or copolymer, a polyaromatic polymer or copolymer, polystyrene polymer or copolymer, ethyl vinylbenzene, ethyl vinylbenzene-divinyl benzene, methylmethacrylate, methacrylate-divinylbenzene, methacrylate-styrene, 2,6-diphenyl-p-phenylene oxide, bonded or non-bonded silica, alumina and fluoracil, said resin having a pore size between 45 to 2000 Å and a surface area between 35 and 2000 m²/g;
  iii. purifying said suspension of step (ii) by a solvent extraction or sonication;
  iv. filtering the suspension through a 0.5 micron filter to remove all particles of sizes below 0.5 micron; and
  v. recovering a fraction remaining on the filter;
 b) vacuum or air drying the fraction remaining on the filter; and
 c) recovering the dry fraction as the sorbent for sampling of the semi-volatile organic gases and particulate components.

2. The method of claim 1, wherein the resin is 2,6-diphenyl-p-phenylene oxide having a pore size 2000 Å and a surface area 35 m²/g.

3. The method of claim 1, wherein the resin is the styrene divinylbenzene copolymer having the pore size 50 Å and the surface area 780 m²/g, or 85 Å and 350 m²/g, or 90 Å and 350 m²/g, or 200 Å and 100 m²/g.

4. The method of claim 1 wherein the resin is the polyaromatic or polystyrene polymer or copolymer.

5. The method of claim 4, wherein the resin is the polyaromatic copolymer having a pore size 500 Å and a surface area 650 m²/g or the polystyrene polymer having a surface area 750 m²/g.

6. The method of claim 1, wherein the resin is ethyl vinylbenzene or ethyl vinylbenzene-divinyl benzene.

7. The method of claim 6, wherein the resin is ethyl vinylbenzene-divinylbenzene having a pore size 45 Å and a surface area 570 m²/g or ethyl vinylbenzene-divinylbenzene having a surface area 735 m²/g.

8. The method of claim 1 wherein the resin is methylmethacrylate, methacrylate-divinylbenzene, or methacrylate-styrene.

9. The method of claim 8, wherein the resin is the methylmethacrylate having a pore size 80 Å and a surface area 450 m²/g or the pore size 250 Å and the surface area 140 m²/g, methacrylate-divinylbenzene having a surface area 320 m²/g or methacrylate-styrene having a surface area 70 m²/g.

10. The method of claim 1, wherein the particles range in size from between 1 and 7 microns.

11. The method of claim 10, wherein a surface to volume ratio of the particles is 200,000 to 4,000 cm⁻¹.

12. The method of claim 10, wherein the sorbent is the combination of the activated carbon and the macroreticular polymeric resin.

13. The method of claim 12, wherein the activated carbon is graphite or black carbon.

14. The method of claim 3 wherein the styrene divinylbenzene copolymer has the pore size 50 Å and the surface area 780 m²/g.

* * * * *